(12) United States Patent
Bernard et al.

(10) Patent No.: US 10,070,912 B2
(45) Date of Patent: Sep. 11, 2018

(54) COUPLING MEANS CONNECTING AN ELECTROSURGICAL INSTRUMENT TO A VACUUM SOURCE, AN ELECTROSURGICAL INSTRUMENT PROVIDED WITH THE COUPLING MEANS, A KIT INCLUDING THE COUPLING MEANS AND THEIR USES

(75) Inventors: Frederic Bernard, Alsgarde (DK); Niels Kornerup, Rungsted (DK); Jesper Schantz Simonsen, Koebenhavn (DK)

(73) Assignee: STRYKER EUROPEAN HOLDINGS I, LLC, Kalamazoo, MI (US)

( * ) Notice: Subject to any disclaimer, the term of this patent is extended or adjusted under 35 U.S.C. 154(b) by 76 days.

(21) Appl. No.: 14/129,909

(22) PCT Filed: Aug. 1, 2011

(86) PCT No.: PCT/DK2011/050300
§ 371 (c)(1),
(2), (4) Date: Dec. 27, 2013

(87) PCT Pub. No.: WO2013/000465
PCT Pub. Date: Jan. 3, 2013

(65) Prior Publication Data
US 2014/0142566 A1    May 22, 2014

(30) Foreign Application Priority Data
Jun. 28, 2011  (DK) .............................. 2011 00482

(51) Int. Cl.
*A61B 18/12*  (2006.01)
*A61B 18/08*  (2006.01)
(Continued)

(52) U.S. Cl.
CPC ............ *A61B 18/085* (2013.01); *A61B 18/10* (2013.01); *A61B 18/1206* (2013.01);
(Continued)

(58) Field of Classification Search
CPC ... A61B 18/085; A61B 18/10; A61B 18/1233; A61B 18/14; A61B 18/1402;
(Continued)

(56) References Cited

U.S. PATENT DOCUMENTS 3,882,862 A  *  5/1975  Berend ...................... A61F 2/06
                                                             138/39
4,002,174 A  *  1/1977  Reed ....................... A61M 39/10
                                                             604/117
(Continued)

FOREIGN PATENT DOCUMENTS

CA     2 299 752       8/2001
GB     2 311 225 A     9/1997
(Continued)

OTHER PUBLICATIONS

English language abstract for JPH07501719 extracted from espacenet.com database on Jul. 31, 2015, 1 page. Also see language equivalent WO93/05721.
(Continued)

*Primary Examiner* — Daniel Fowler
(74) *Attorney, Agent, or Firm* — Howard & Howard Attorneys PLLC

(57) ABSTRACT

A coupling means (8;8';8",14) serves for connecting a suction channel (27) of an electrosurgical instrument (1) to a vacuum source via a suction tubing (11) and/or for guiding an electrical cable (12), that supplies electrical energy from an electrosurgical generator to the electrosurgical instrument (1). The electrosurgical instrument (1) comprises a hollow elongated main body (2) having a first end (7) for securing
(Continued)

Figure 1:
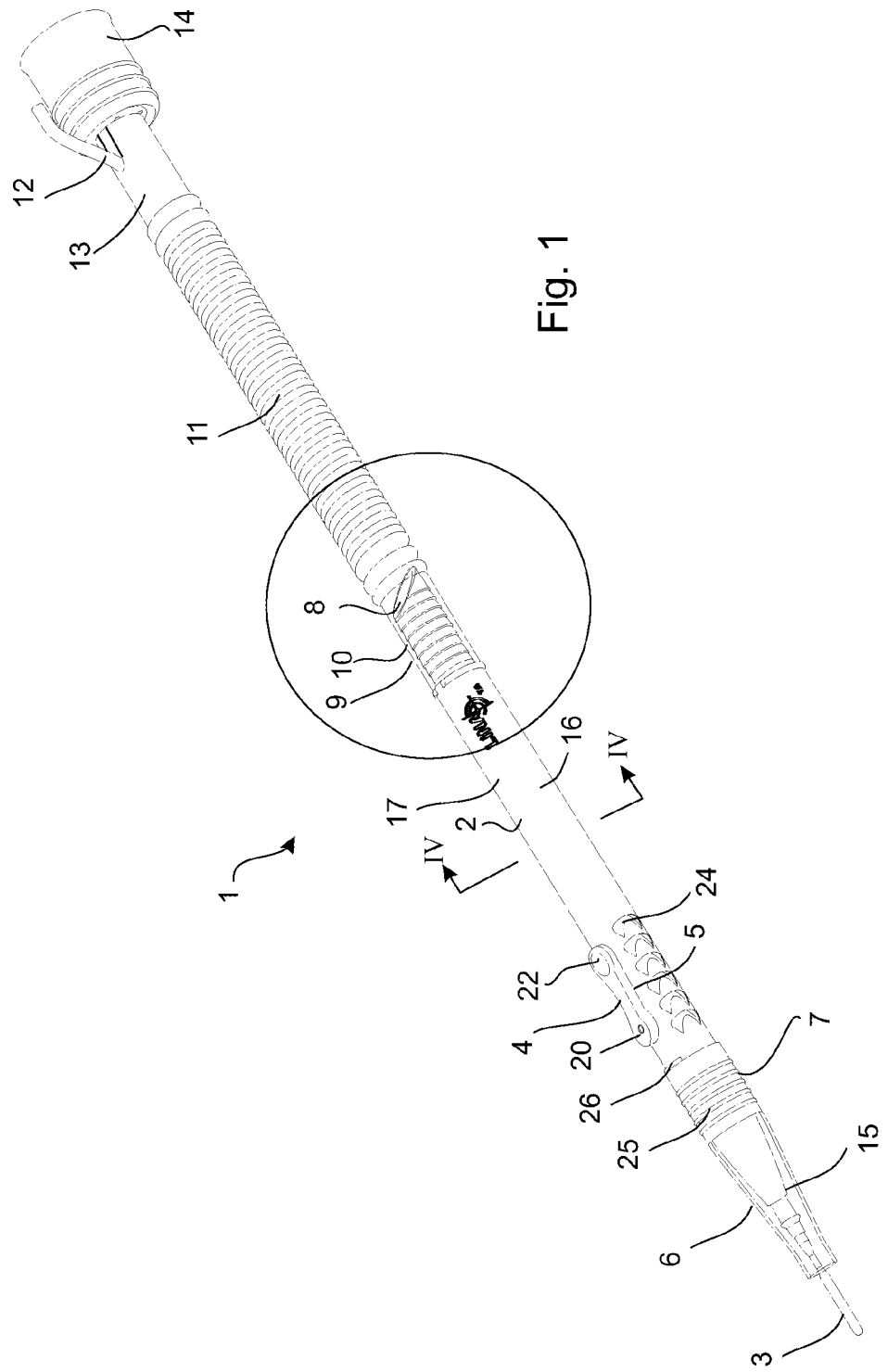

a first means (3) for application of the electrical energy to a surgical site and an opposite second end (9), which hollow elongated main body (2) has a switch means (5) to be operated by means of an associated actuator (4) to control application of the electrical energy to the surgical site. The coupling means (8;8';8") comprises at least a first coupling part (8;8';8") for inserting between the second end (9) of the hollow elongated main body (2) and the suction tubing (11), which first coupling part (8;8';8") is configured to attach the suction tubing (11) in tandem with said hollow elongated main body (2) and/or to accommodate the electrical cable (12) exiting the hollow elongated main body (2) along the longitudinal axis of said first coupling part (8;8';8"). A kit including the coupling means and other components for an electrosurgical instrument is also disclosed.

8 Claims, 13 Drawing Sheets

(51) Int. Cl.
*A61B 18/14* (2006.01)
*H01H 23/06* (2006.01)
*A61B 18/18* (2006.01)
*A61B 18/10* (2006.01)
*A61B 18/00* (2006.01)

(52) U.S. Cl.
CPC .......... *A61B 18/1402* (2013.01); *A61B 18/18* (2013.01); *H01H 23/06* (2013.01); *A61B 2018/0094* (2013.01); *A61B 2018/00172* (2013.01); *A61B 2018/00922* (2013.01); *A61B 2018/00958* (2013.01); *A61B 2218/008* (2013.01)

(58) Field of Classification Search
CPC ........ A61B 18/1442; A61B 2018/0013; A61B 2018/00559; A61B 2018/00601; A61B 2018/00642; A61B 2018/00708; A61B 2018/00755; A61B 2018/00875; A61B 2018/126; A61B 2018/1286; A61B 2018/1407; A61B 2018/1412; A61B 2039/1016; A61B 2039/1022; A61B 2039/1027; A61B 2039/1038; A61B 2039/1044; A61B 2039/1061; A61B 2039/1066; A61B 2039/1077; A61M 39/10; A61M 39/1011; A61M 39/105
See application file for complete search history.

(56) References Cited

U.S. PATENT DOCUMENTS

| | | | | |
|---|---|---|---|---|
| 4,204,328 A | * | 5/1980 | Kutner | A61M 1/008 15/418 |
| 4,211,439 A | * | 7/1980 | Moldestad | F16L 37/113 285/27 |
| 4,511,163 A | * | 4/1985 | Harris | A61M 39/10 285/148.16 |
| 4,960,419 A | * | 10/1990 | Rosenberg | A61B 18/1402 30/296.1 |
| 5,085,657 A | | 2/1992 | Ben-Simhon | |
| 5,098,430 A | | 3/1992 | Fleenor | |
| 5,176,415 A | * | 1/1993 | Choksi | A61M 39/10 128/202.27 |
| 5,451,223 A | * | 9/1995 | Ben-Simhon | A61M 1/0084 604/35 |
| 5,496,314 A | | 3/1996 | Eggers | |
| 5,681,063 A | * | 10/1997 | Bressner | A61M 39/1011 285/123.1 |
| 5,839,715 A | * | 11/1998 | Leinsing | A61J 1/2096 251/149.1 |
| 5,967,569 A | * | 10/1999 | Vaillancourt | A61M 39/12 285/295.2 |
| 6,146,353 A | | 11/2000 | Platt, Jr. | |
| 6,524,307 B1 | * | 2/2003 | Palmerton | A61B 18/00 604/22 |
| 8,684,979 B2 | * | 4/2014 | Deighan | A61M 39/10 285/332.5 |
| 2003/0028182 A1 | * | 2/2003 | Abboud | A61B 18/02 606/21 |
| 2004/0220561 A1 | * | 11/2004 | Kirwan, Jr. | A61B 18/12 606/41 |
| 2005/0137581 A1 | * | 6/2005 | Azar | A61M 1/008 604/542 |
| 2005/0245899 A1 | | 11/2005 | Swisher | |
| 2007/0060898 A1 | * | 3/2007 | Shaughnessy | A61M 39/10 604/284 |
| 2008/0077176 A1 | * | 3/2008 | Hanlon | A61H 9/0078 606/201 |
| 2008/0294154 A1 | * | 11/2008 | Ibrahim | A61B 18/1492 606/13 |
| 2009/0018539 A1 | | 1/2009 | Cosmescu | |

FOREIGN PATENT DOCUMENTS

| | | |
|---|---|---|
| JP | H07501719 A | 2/1995 |
| JP | 2001046385 A | 2/2001 |
| JP | 2007532274 A | 11/2007 |
| WO | WO93/05721 | 4/1993 |
| WO | WO 2005/046498 A1 | 5/2005 |

OTHER PUBLICATIONS

English language abstract for JP 2001046385 extracted from espacenet.com database Nov. 10, 2016, 1 page.
English language abstract not found for JP 2007532274; however, see English language equivalent US20050245899.

* cited by examiner

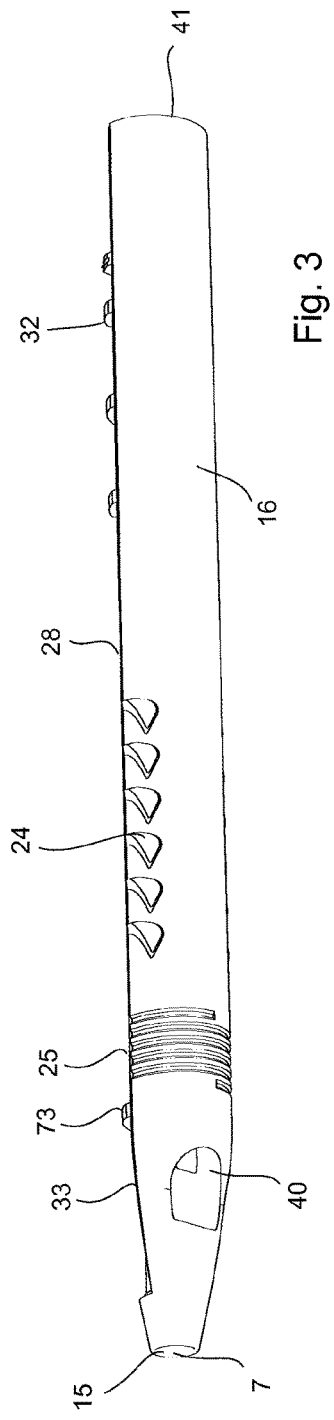
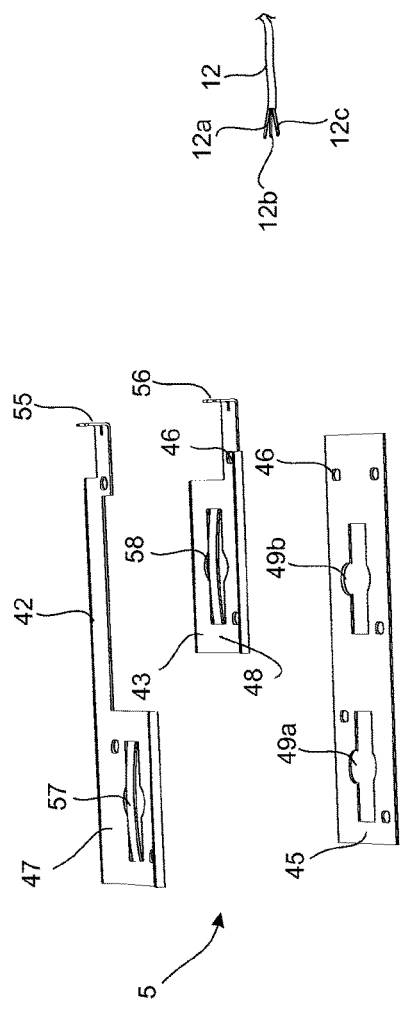
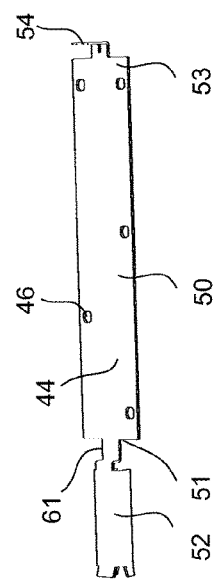
Fig. 3
Fig. 5

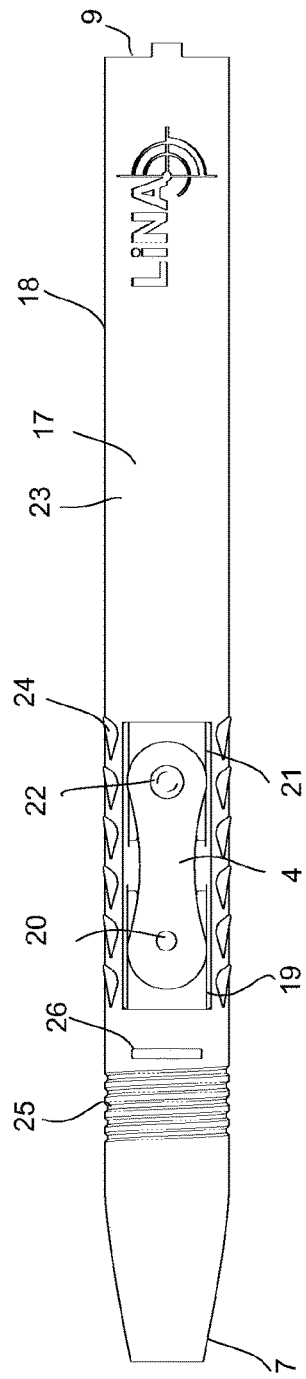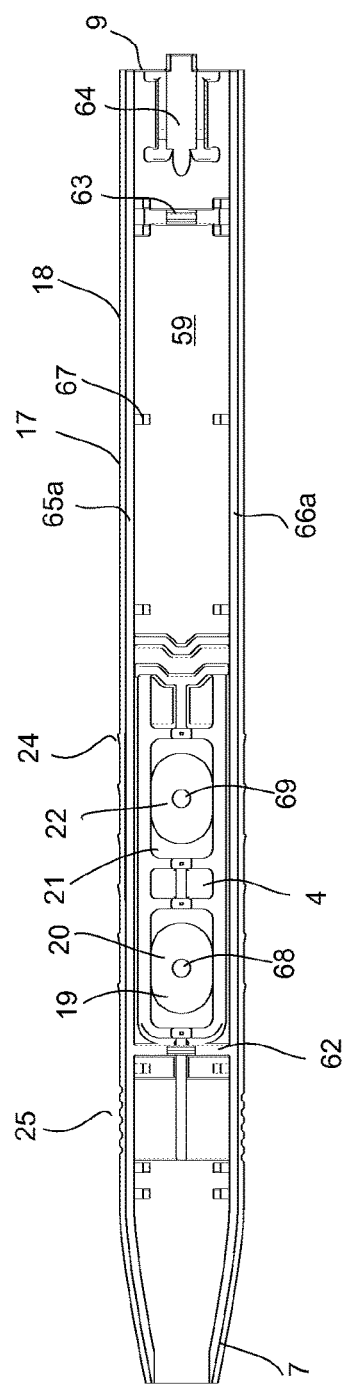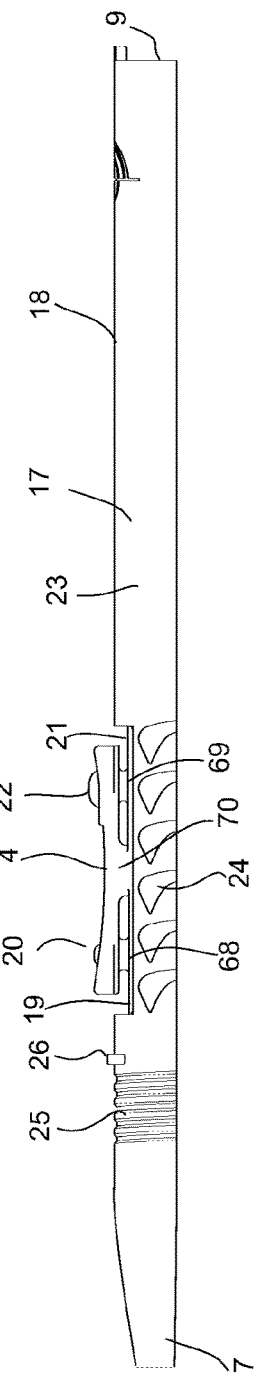

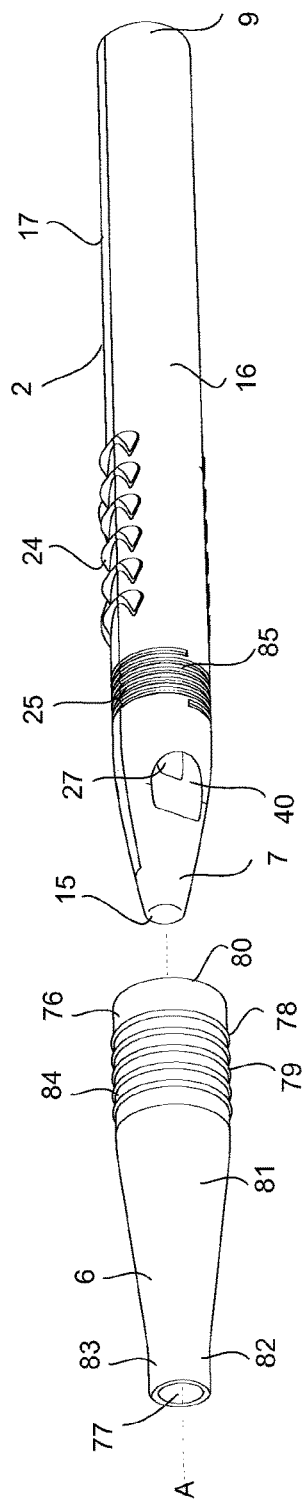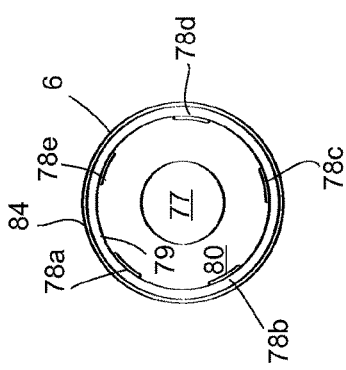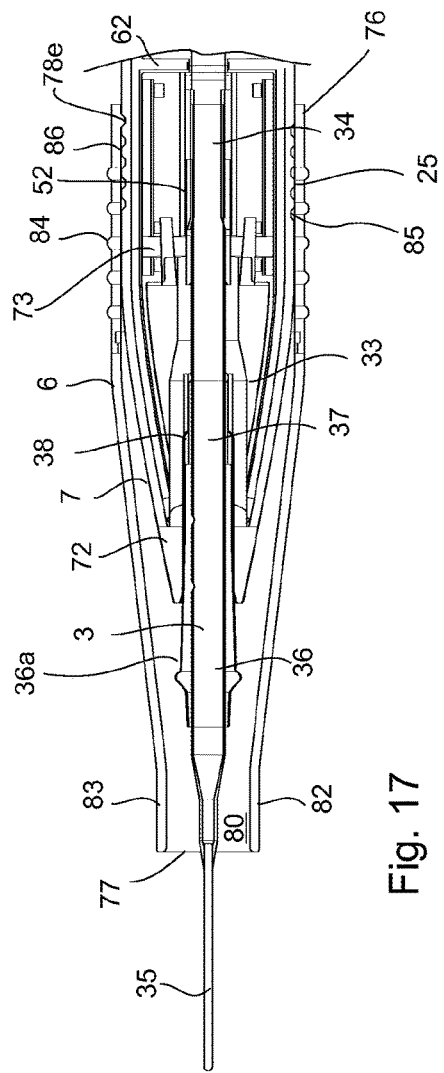

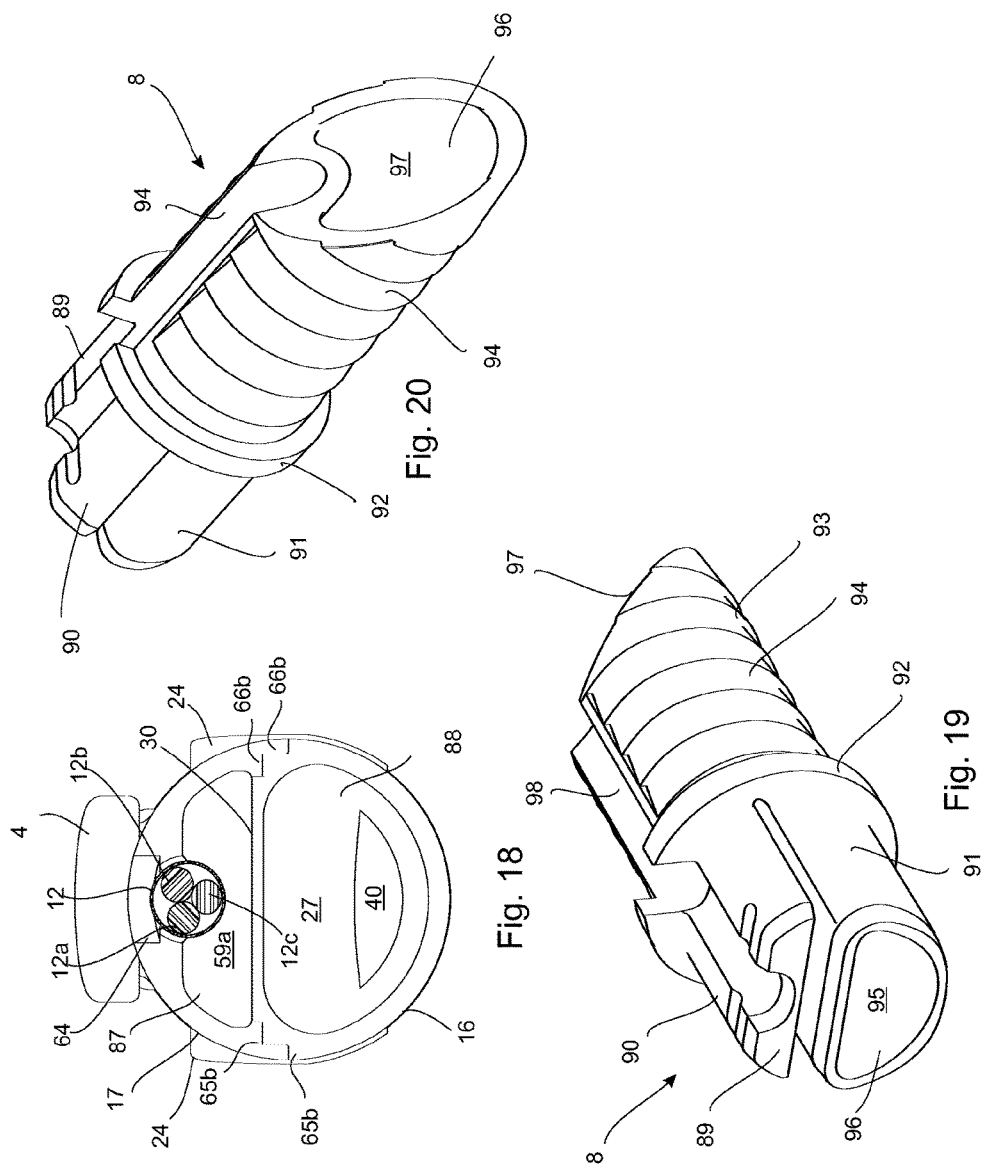

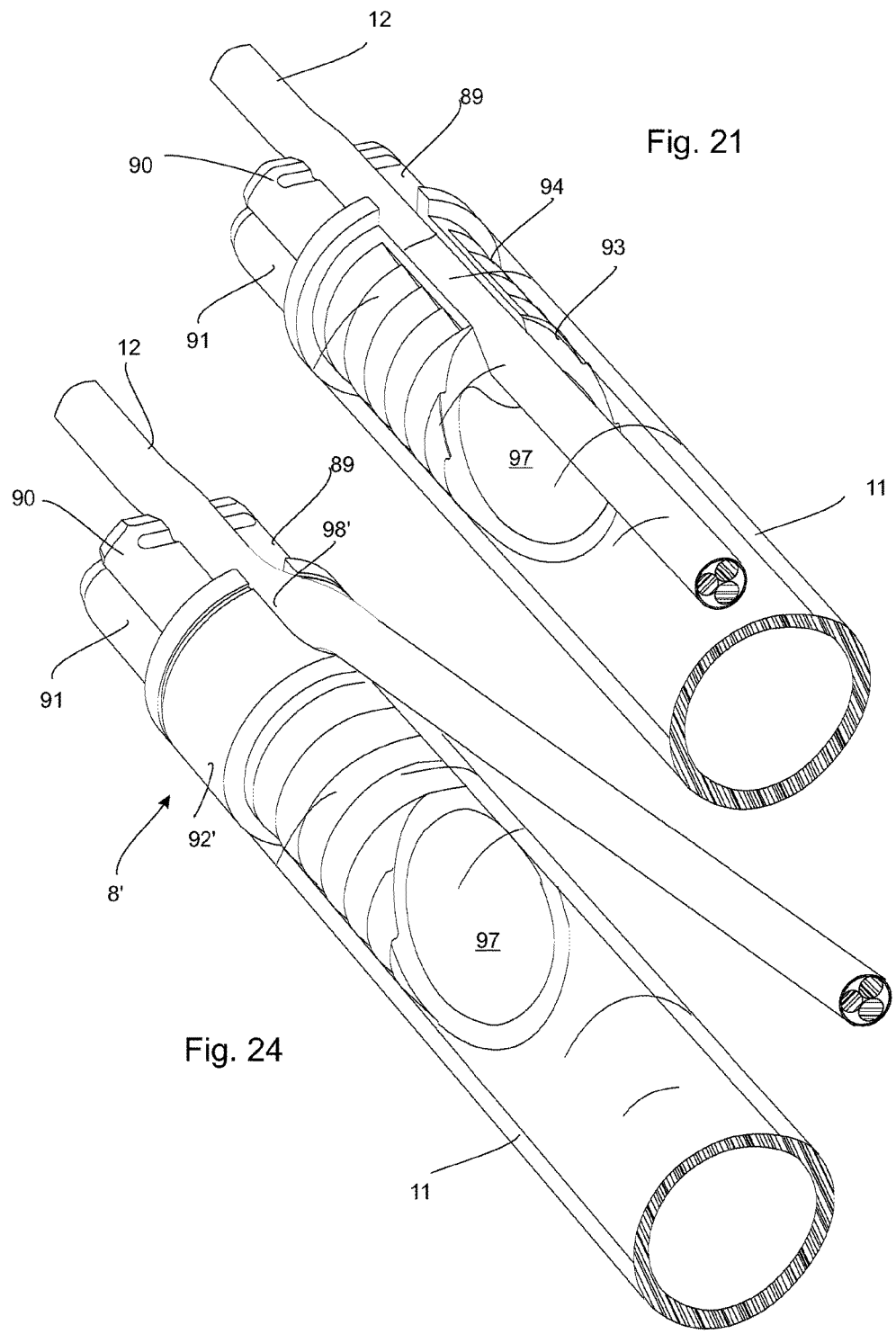

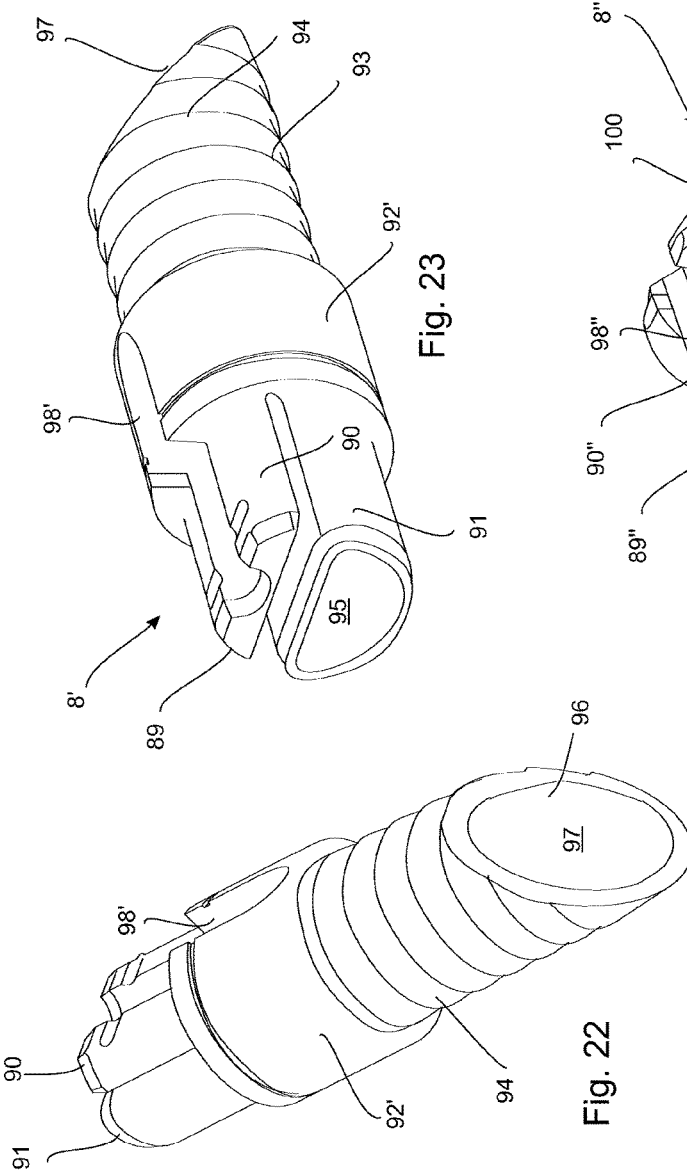

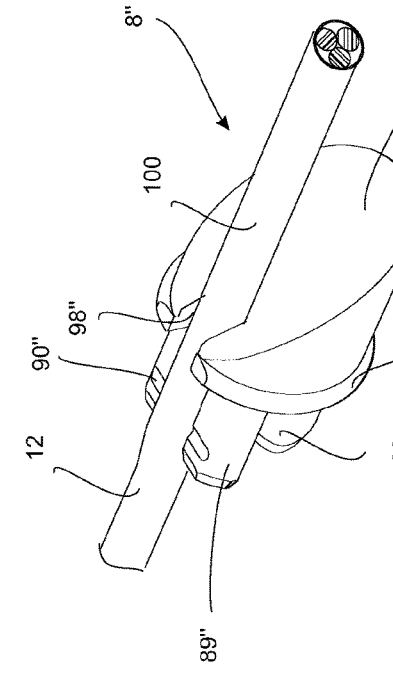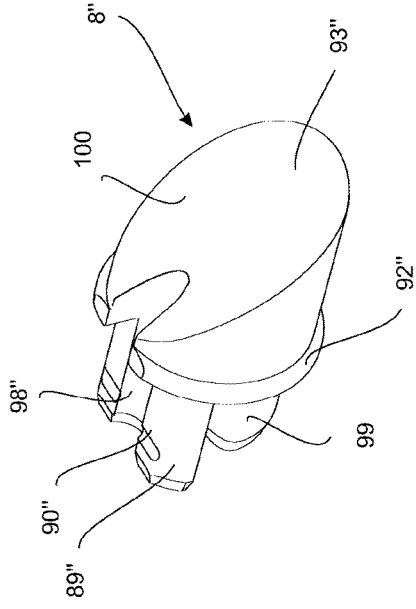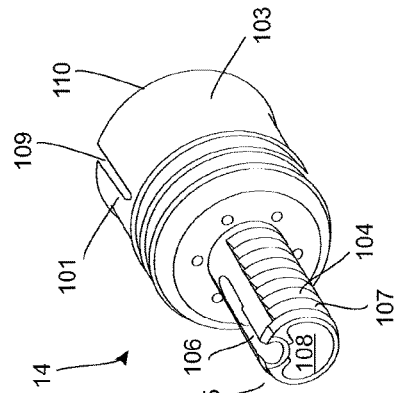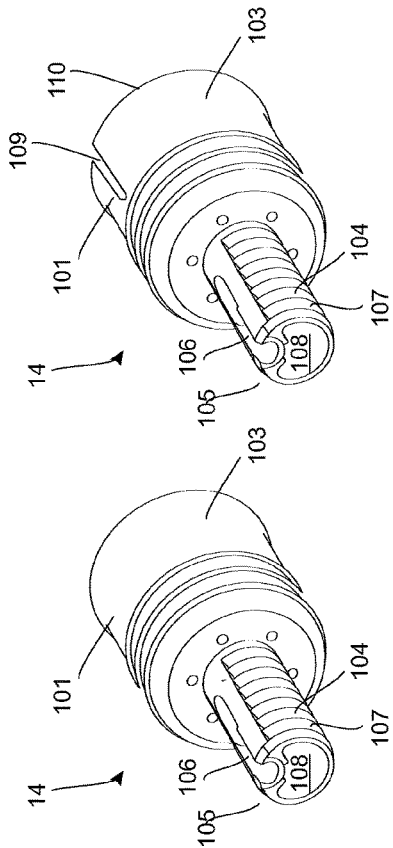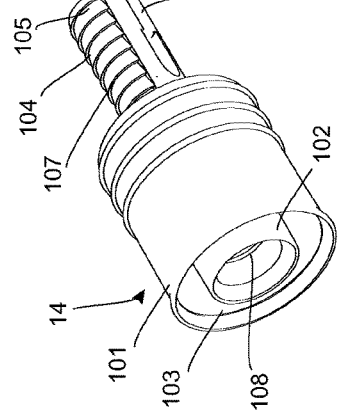
Fig. 26
Fig. 27
Fig. 28
Fig. 29
Fig. 30

COUPLING MEANS CONNECTING AN ELECTROSURGICAL INSTRUMENT TO A VACUUM SOURCE, AN ELECTROSURGICAL INSTRUMENT PROVIDED WITH THE COUPLING MEANS, A KIT INCLUDING THE COUPLING MEANS AND THEIR USES

The present invention relates to a coupling means for connecting a suction channel of an electrosurgical instrument to a vacuum source via a suction tubing and/or for guiding an electrical cable that supplies electrical energy from an electrosurgical generator to the electrosurgical instrument. The electrosurgical instrument comprises a hollow elongated main body having a first end for securing a first means for application of the electrical energy to a surgical site and an opposite second end, which elongated main body has a switch means to be operated by means of an associated actuator to control application of the electrical energy to the surgical site.

In electrosurgery high frequency (radio-frequency) current is applied by an active electrosurgical electrode to cause a cutting action, hemostasis, or coagulation of bleeding tissue. This procedure produces smoke and coagula resulting in a decreased visibility of the operative field. Electrosurgical smoke plume in high concentrations is considered hazardous and causes health care problems. Thus the reasons for facilitating effective and instantaneously evacuation of such side products are numerous and various approaches have been suggested to remedy the problems.

Some prior art elongated electrosurgical instrument has no suction channel, in which case the elongated electrosurgical can appear slim and handy. In case the instrument needs to be combined with suction, a suction channel is clicked on the outside of the elongated electrosurgical instrument, thereby making the combined instrument very thick, ponderous and difficult to handle. Detachable, exterior suction channels are less preferred by surgeons. As an example U.S. Pat. No. 6,146,353 discloses a smoke extraction device for use with an electrosurgical instrument. The smoke extraction device includes an elongated body portion. An attachment member serves for releasably securing the smoke extraction device exterior to the surgical instrument and in parallel thereby making the assembled instrument thick, large, clumsy and inconvenient to use for the surgeon. A substantially similar arrangement is known from U.S. Pat. No. 5,085,657.

Thus there remains a need within the art for improved and user-friendly ways to secure a suction tubing to an electrosurgical instrument. There also remains a need within the art for having the electrical cable and the suction tubing under control when using the electrosurgical instrument.

Accordingly, it is a main aspect of the present invention to provide a coupling means and an electrosurgical instrument of the kind mentioned in the opening paragraph, which electrosurgical instrument meets the above needs.

It is a second aspect of the present invention to provide an electrosurgical instrument, which has an integral suction channel but nevertheless can be used both with and without suction.

It is a third aspect of the present invention to provide an electrosurgical instrument, which has an ergonomic design and does not require use of a detachable suction channel in parallel with the hollow elongated main body for evacuation of matter from a surgical site.

It is a fourth aspect of the present invention to provide a coupling means for securing a suction tubing to an electrosurgical instrument.

It is a fifth aspect of the present invention to provide a coupling means comprising multiple coupling parts that fit together with a single hollow elongated main body.

It is a sixth aspect of the present invention to provide a simple and versatile coupling means including a coupling part fitting on vacuum source pipe connections of more than one diameter.

The novel and unique features whereby these and other aspects are achieved according to the present invention consist in that the coupling means comprises at least a first coupling part for inserting between the second end of the hollow elongated main body and the suction tubing, which first coupling part is configured to attach the suction tubing in tandem with said hollow elongated main body and/or to accommodate the electrical cable exiting the hollow elongated main body along the longitudinal axis of said first coupling part.

Within the context of the present invention the term "in tandem" means that the first coupling part is mounted behind the elongated hollow main body. Thus, the first coupling part extends in series with and in axial elongation of the hollow elongated main body. A suction tubing is coupled in elongation of the hollow elongated main body despite the fact that the electrical cable also needs to be externalised from the hollow elongated main body. Thus, by means of the first coupling part according to the present invention a suction tubing can be placed in series with the hollow elongated main body, and needs not extend in parallel below the hollow elongated main body as in the prior art systems. Because the electrical cable is accommodated in or at the first coupling part, the electrical cable is guided when exiting the second end of the hollow elongated main body. In this manner both an electrical cable and a suction tubing can be kept away from the first end of the electrosurgical instrument, and thus not in the surgeon's way when operating.

If an electrosurgical instrument is to be used with a vacuum source the first coupling part is expediently inserted at the second end of the hollow elongated main body to keep control of the cable as well as the suction tubing.

Advantageously, the first coupling part may have a first plug end part fitting into the second end of the hollow elongated main body and an opposite second plug end part that fits into the suction tubing, said first plug end part may comprise a first protruding leg being a first click-in part fitting into a first click-in opening of a first compartment of the hollow elongated main body through which the cable is externalised, and a second click-in part being a second protruding leg fitting into a second click-in opening of the suction channel of the hollow elongated main body.

Accordingly, the first coupling part serves as an intermediate member that is inserted for e.g. coupling the electrosurgical instrument to a suction tubing for a vacuum source or just for guiding and/or securing the electrical cable at the second end of the hollow elongated main body. The first click-in part and the second click-in part may both be male parts that easily can be plugged into respective female openings of the first compartment and the suction channel simply by being clicked-in into the second end of the hollow elongated main body. Acceptable coupling efficiency may be improved by snap-fitting due to presence of snap-fitting features, such as e.g. key and slot, or be satisfactorily just due to firm frictional engagement.

The first click-in part and the second click-in part may be substantially parallel parts of same or different lengths to allow the first coupling part to follow the shape and exterior outline of the hollow elongated main body when inserted into its second end. A smooth transition between first coupling part and the hollow elongated main body can be obtained. Setoffs and projections at the second end of the hollow elongated main body can expediently be substantially avoided, as well as the need for attaching a separate suction channel coaxially below the hollow elongated main body is eliminated. The lengths of the click-in parts contribute to firm fitting and to guide the first coupling part properly in place.

In one embodiment of the first plug end part the first click-in part can be end-closed or has a blind end to avoid access of dirt and other matter into the first compartment. The first click-in part may be solid or hollow. In the latter case the first click-in part may be constituted by a tubular hollow leg end-closed by a terminal end face or be blinded by the provision of a blind face disposed further inside the tubular hollow leg.

In the same embodiment or a further embodiment of the first plug end part, the second click-in part and the second plug end part can both be hollow, thereby defining an evacuation pathway through the first coupling part. This evacuation pathway has a suction inlet at the second click-in part and a suction outlet at the second plug end part in order to put the suction channel of the electrosurgical instrument in fluid communication with the vacuum source via the suction tubing.

In case the electrosurgical instrument is used in a surgical procedure that does not require suction the surgeon may choose a first plug end part configured so that at least one of the second click-in part and the second plug end part are end-closed or has a blind end, thereby being able to quickly modify the electrosurgical instrument that previously was intended for use with a suction means to be used without suction means, e.g. as a simple surgical pencil. An end-closed or blinded second click-in part and/or second plug end part serves to close the suction channel at the second end of the hollow elongated main body. It should be understood that the evacuation pathway can be closed or blinded by the provision of an interior partition wall, as well as by means of end faces at any or both of the suction inlet and the suction outlet. Alternatively, any of the second click-in part and the second plug end part can be solid.

The second plug end part can be bevelled to facilitate its guiding into a first opening of the suction tubing. Optionally the second plug end part may have coupling barbs provided on the exterior side. The coupling barbs serve to catch and engage the interior side of the suction tubing to ensure that the suction tubing does not detach once negative pressure is applied by the vacuum source. The coupling barbs may expediently taper towards the suction outlet, which tapering facilitates mounting of the first end of the suction tubing due to the free end of the second plug end part can be given an exterior cross-section or diameter slightly smaller than the internal diameter of the suction tubing. Alternatively, said exterior cross-section is the same or slightly larger than the internal diameter of the suction tubing, and the suction tubing is made of a material that is able to yield sufficiently to be fitted over the second plug end part but not to yield more than a tight seal can be preserved.

The first coupling part can have a circumferential collar disposed between the first plug end part and the second plug end part. The circumferential collar serves as a stop means to prevent the first coupling part from being pushed too far inside the hollow elongated main body, and to some extent also to avoid that the suction tubing it pushed too close to the hollow elongated main body so that the cable thereby is affected, e.g. is pushed or bend towards the second end of the hollow elongated main body. When the first coupling part is inserted en the hollow elongated main body the circumferential collar abuts the second end of the hollow elongated main body at the side facing the first plug end part. The opposite side of the circumferential collar may abut the suction tubing.

To allow the cable to exit substantially flush with the exterior face of the annular wall of the hollow elongated main body, the first plug end part may have a first cable groove that extends in the longitudinal direction of the first plug end part for accommodating the cable when the first click-in part is mounted inside the first click-in opening. Accommodation of the cable inside a first cable groove allows the cable to be externalised at the second end of the hollow elongated main body without provision of further cable exit apertures, slots or holes in the hollow elongated main body for that purpose. Finally, the first cable groove ensures that the cable cannot bend or kink.

The first click-in part may hold the short length of the cable, that extends coaxially, pressed towards the interior face of the annular wall of the hollow elongated main body to aid in prevent axial displacement of both cable and first coupling part.

The first cable groove can be provided so that it extends along at least a length of the first click-in part or to extend along the entire length of the first click-in part and at least partly along the axial length of the annular collar. In these embodiments the cable is able to exit the first coupling part via the first guide groove where said first cable groove ends, in order to extend further outside the suction tubing. The surgeon may also choose to use the electrosurgical instrument without suction, in which case the first coupling part just plugs and closes the first click-in opening and the second click-in opening of the hollow elongated main body and traps the cable inside the first cable groove.

Alternatively, the first cable groove can be provided along the entire length of the first coupling part, through the annular collar and further along the second coupling end part. In this embodiment of a first coupling part the cable is able to pass from inside the hollow elongated main body out of the second opening of the hollow elongated main body, via the first coupling part inside the suction tubing via its first end, while being bedded into the first cable groove. The cable then passes inside said suction tubing until it exits at the suction tubing's opposite second end. By confining the cable inside the suction tubing the cable is conveniently combined with the suction tubing along its entire length. The cable and suction tubing are made to be one single unit, thereby relieving the surgeon from some of the burden of controlling and organising the surgical equipment. The cable cannot become entangled with or catch other components, such as the suction tubing, a surgical drape, another instrument or any other components present at the surgical site while being hidden inside the suction tubing.

Depending on the kind of electrosurgical instrument the surgeon needs or prefer he/she can chose between the various embodiments of first coupling parts according to the present invention, e.g to allow the cable and the suction tubing to be combined so that the cable is either inside or outside the suction tubing, or if the electrosurgical instrument is to be used without suction.

The first cable groove may advantageously have a first cross-section corresponding substantially to the cross-section of the cable, optionally larger than the cross-section of the cable, so that the cable can fit into the first cable groove and the suction tubing be suitable mounted at the second plug end part. The coupling means may comprise a second coupling part for attaching the suction tubing to the vacuum source, which second coupling part conveniently may have a suction tubing end part for securing to the suction tubing and an opposite second coupling end part for attaching the suction tubing to the vacuum source, which second coupling end part comprises an inner tube and an outer tube of larger internal diameter than the inner tube. The second coupling end part fits over connection pieces of two different diameters. Thus there are two options, not only one, for connecting the suction tubing to an available vacuum source. Vacuum sources are provided with two different standard diameters of connection pieces, and often the surgeon experiences that the available connection piece does not match the coupling part already present at the suction tubing of the instrument he/she is about to use. Or, if no coupling part is present at the second end of the suction tubing, that the diameter of the suction tubing is wrong for the connection piece. Instead of inserting unpractical or home-made adapters or replacing the vacuum source or the suction tubing, the arrangement of the duplex tubing of the second coupling part offers the possibility of coupling the suction tubing to two different connection pieces on the same or different vacuum sources using just one and the same single coupling part.

In a preferred embodiment of the second coupling part the inner tube and the outer tube are substantially concentric so that the act of centring of the second coupling part in relation to the connection piece are substantially the same irrespective of the diameter of the available connection piece.

In case the second coupling part is used with a suction tubing having a cable extending inside, the suction tubing end part can beneficially have an annular wall with a second cable groove to guide the cable when exiting the suction tubing and allow the second end of the suction tubing to pass over and be fitted around the suction tubing end part, as also described for the first coupling part.

The second cable groove may have a second cross-section corresponding substantially to the cross-section of the cable, optionally larger than the cross-section of the cable to accommodate the cable in the same manner as described for the first coupling part.

Although described in relation to the coupling means according to the present invention emphasis is made that the second coupling part can be used for any kind of suction instrument requiring a suction tubing to be connected to a vacuum source.

As mentioned above any of the first coupling part and/or the second coupling part can be detachably inserted into the suction tubing, however any of the first coupling part and the second coupling part may alternatively be preinserted at the respective ends of the suction tubing, or be detachably mounted to the suction tubing. The first coupling part can also be detachable from the hollow elongated main body.

The different embodiments of first coupling parts and the second coupling part can be provided as accessories to be assembled later with one or more of the electrosurgical instrument, electrosurgical generator, suction tubing and vacuum source.

In a preferred embodiment of the second coupling part according to the present invention the outer tube of the second coupling part has at least one longitudinal slot provided in it's annular wall. The at least one longitudinal slot extends from a free end of the outer tube towards the suction tubing end part. The slot has opposite free edges that can be brought to overlap to reduce the diameter of the outer tube so that said outer tube fits inside a connection piece of a vacuum source instead of being fitted outside connection pieces. Thus vacuum sources having standard connection pieces of e.g. 8-22 mm can easily be fitted together with the second coupling part according to the present invention.

The invention also relates to an elongated electrosurgical instrument comprising a hollow elongated main body having a first end for securing a first means for application of electrical energy to a surgical site and an opposite second end, which hollow elongated main body has a switch means to be operated by means of an associated actuator, to control application of the electrical energy to the surgical site, and a coupling means, as described above, for connecting a suction channel of the electrosurgical instrument to a vacuum source via a suction tubing and/or for guiding an electrical cable, that supplies the electrical energy from an electrosurgical generator to the electrosurgical instrument.

The hollow elongated main body may have a longitudinal extending partition wall that divides said hollow elongated main body in an elongated first compartment for accommodating at least the switch means and a second compartment constituting the suction channel whereby the elongated first compartment has been provided with a first click-in opening for receiving a first protruding leg being a first click-in part of a first plug end part of the first coupling part, and the suction channel has been provided with a second click-in opening, for receiving a second protruding leg being a second click-in part of a first plug end part of the first coupling part. The space between the protruding first click-in part and the protruding second click-in part serves for receiving the partition wall at the second end of the hollow elongated main body.

The invention further relates to an assembly kit comprising an electrosurgical instrument with a suction channel to be connected to a vacuum source via a suction tubing and/or for guiding an electrical cable, that supplies electrical energy from an electrosurgical generator to the electrosurgical instrument.

The assembly kit comprises one or more of
- a hollow elongated main body configured with a switch means to be operated by an actuator associated with the hollow elongated main body, a cable for supplying electrical energy from an electrosurgical generator to a first means for at least cutting and/or coagulation of tissue,
- at least one suction tubing,
- at least one first coupling part as defined in any of the preceding claims for securing the suction tubing to the second end of the hollow elongated main body, and
- at least one second coupling part as defined in any of the preceding claims for connecting the suction tubing to the vacuum source.

The at least one first coupling part included in the assembly kit may be selected from first coupling parts having one or more of the following structural features alone or in combination:
- a first plug end part with a first protruding leg being a first click-in part fitting into a first click-in opening of a first compartment of the hollow elongated main body through which the cable is externalised, and a second protruding leg being a second click-in part fitting into a second click-in opening of the suction channel of the hollow elongated main body,
- a first cable groove extending along the entire lengths of the first coupling part, a first cable groove extending along a part of the length of the first coupling part,
the first click-in part is end-closed or blind,
the second click-in part is end-closed or blind,
the second click-in part is hollow,
the second plug end part is end-closed or blind,
the second plug end part is hollow,
the second plug end part is bevelled, and
the second plug end part has coupling barbs provided on the exterior side.

These structural features can be combined to manufacture any conceivable first coupling part for use with one and the same hollow elongated main body of an electrosurgical instrument; the cable can extend inside a suction tubing, outside a suction tubing, the same instrument can be used without suction at all, and at no time the tight sealing between the second end of the hollow elongated main body and the first coupling part is compromised. The coupling force between the hollow elongated main body, the first coupling part and the suction tubing is high and can resist even very high negative pressure during use with a vacuum source, without the risk of getting apart.

The assembly kit according to the present invention may include further components, e.g. various interchangeable first means, in the form of electrosurgical electrodes, including the below described blade electrode with a securing part of pentagonal cross-section, and the below described suction tips of various length and design.

The kit enables assembling of exactly the electrosurgical instrument the surgeon needs and/or prefers, and to make individual modifications of same. Providing the electrosurgical instrument as a kit makes the electrosurgical instrument versatile, and the surgical clinic or hospital needs only to have the kits at stock in order to also have inexpensive access to a plurality of different electrosurgical instruments. Components of the kit can be provided as a separate kit including all possible components, or as individual bulk components, so that a hospital can establish a storage of spare part.

Further, the invention relates to a use of the coupling means as described above for connecting an electrosurgical instrument having a suction channel to a vacuum source.

Yet further, the invention relates to the use of a coupling means for modifying an electrosurgical instrument having a suction channel for use without suction.

Figure 2:
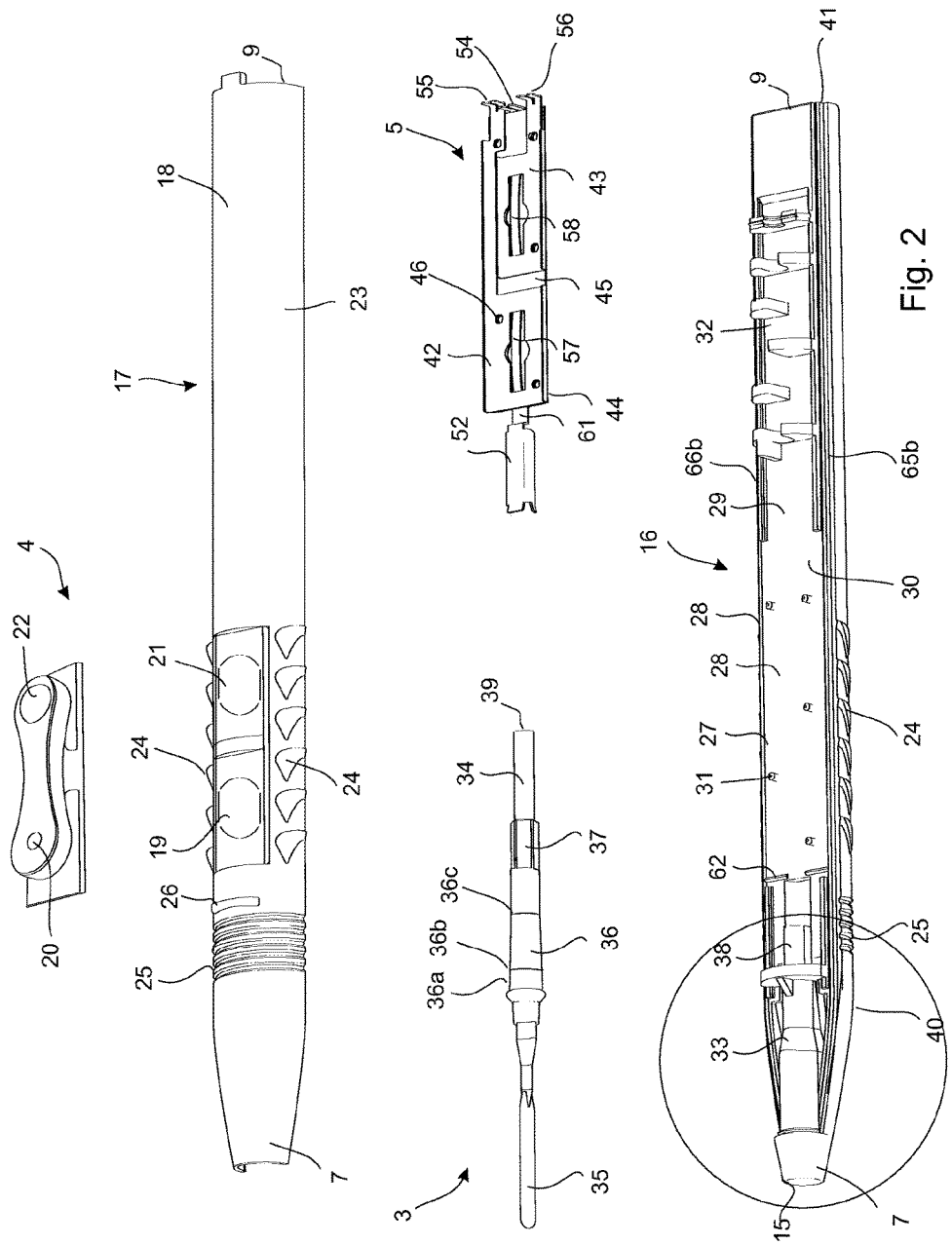
Figure 6:
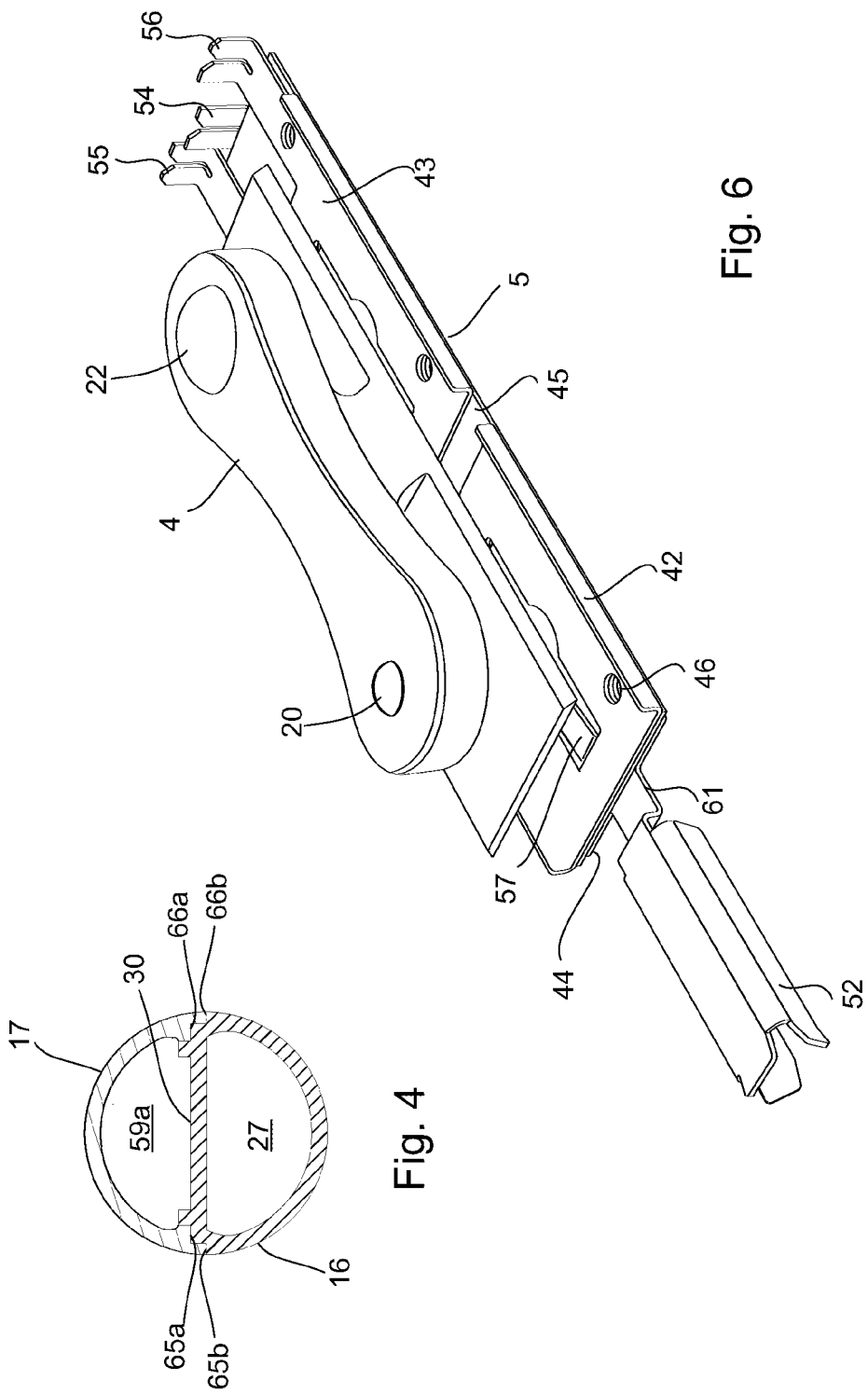
Figure 7:
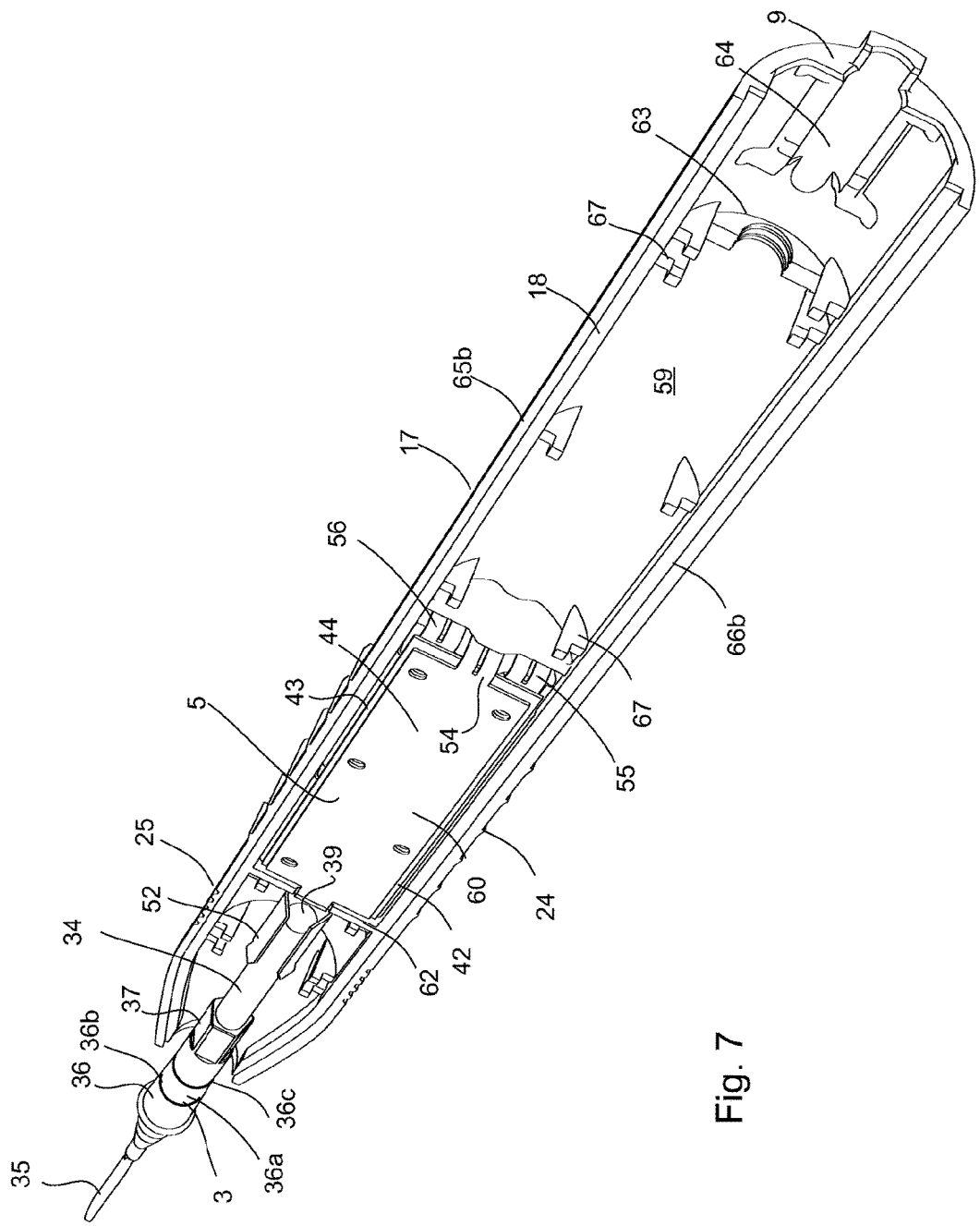
Figure 11:
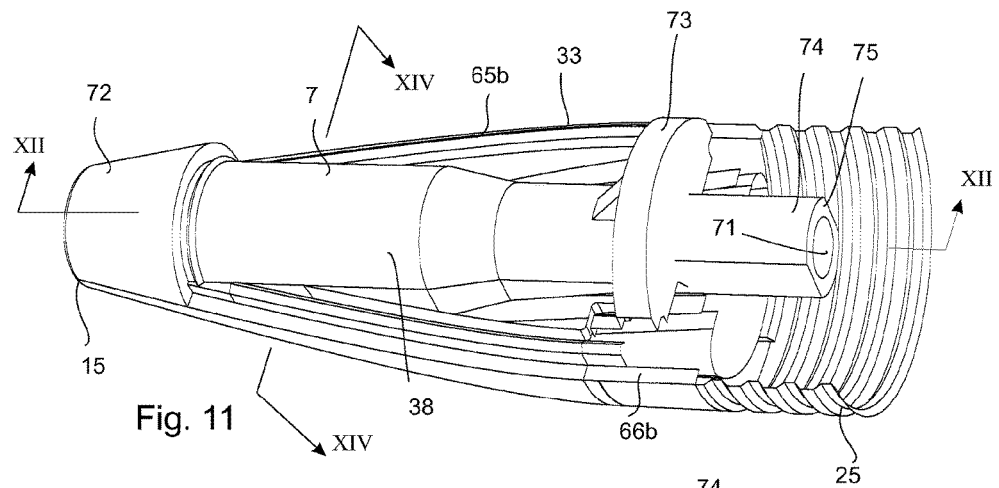
Figure 12:
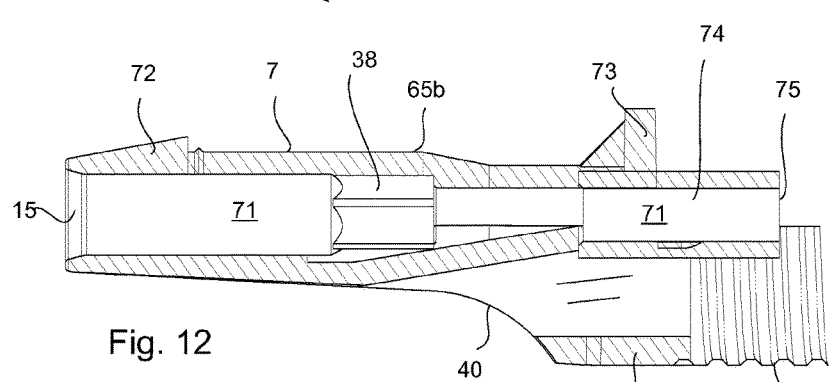
Figure 13:
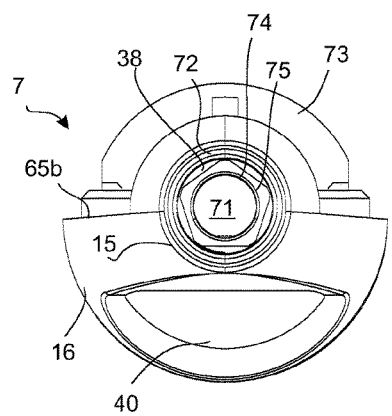
Figure 14:
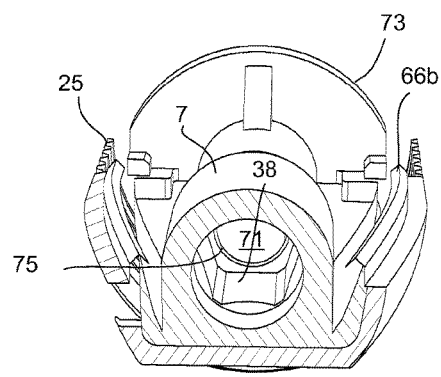
Figure 31:
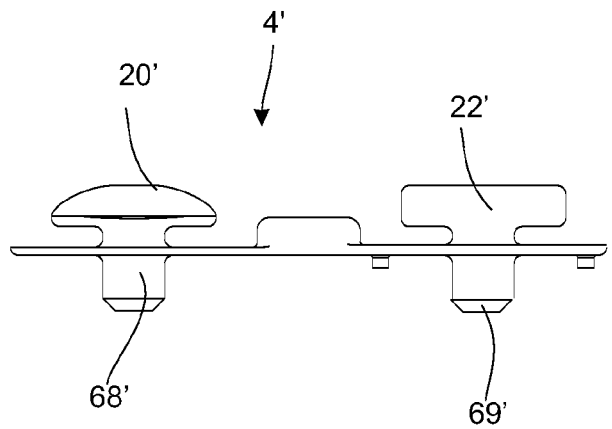
Figure 32:
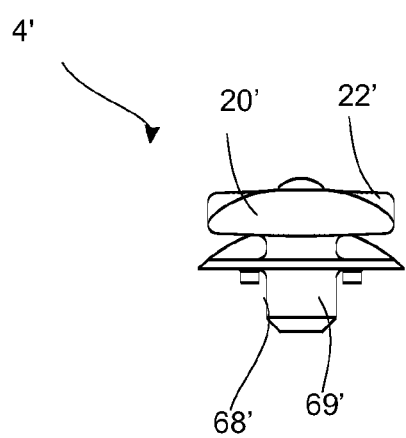

FIG. 1 shows a perspective top view of a first embodiment of an elongated electrosurgical instrument according to the present invention, FIG. 2 shows the elongated main body, the first means, and the switch means in an exploded, enlarged scale perspective view, FIG. 3 shows the tubular part of the first embodiment shown in FIG. 1 in a perspective view seen from below, FIG. 4 is a sectional view of the elongated main body shown in FIG. 1 taken along line IV-IV illustrating the joining of the tubular part and the cover part, but without the cable, FIG. 5 shows an exploded, perspective view of the switch means and a fragment of an associated cable, FIG. 6 shows an enlarged scale view of the switch means in assembled state with an actuator arranged above, FIG. 7 shows a perspective view seen inside the cavity of the cover part, wherein the switch means and the first means has been inserted, FIG. 8 is a top view of the cover part, FIG. 9 is a view inside the elongated cavity of the cover part provided with the actuator, FIG. 10 shows the cover part seen from the side, FIG. 11 is a fragmentary, enlarged scale view of the first end of the tubular part encircled in FIG. 2, FIG. 12 is an axial sectional view taken along line XII-XII in FIG. 11, FIG. 13 shows the tubular part seen through the first end of the elongated main body, and prior to inserting the first means, FIG. 14 is an oblique, cross-sectional view taken along line XIV-XIV in FIG. 11 seen from the first end of the tubular part, FIG. 15 is a perspective view of the suction tip in front of the elongated main body, FIG. 16 is an end view of the suction tip seen inside the bore of the suction tip from the coupling end part, FIG. 17 is an enlarged scale axial, sectional view of the front end of the tubular part provided with a suction tip, FIG. 18 shows the elongated main body seen from the second end with a fragment of a cable, FIG. 19 is a perspective view seen oblique from a first plug end part of a first embodiment of the first coupling part used in the electrosurgical instrument seen in FIG. 1, FIG. 20 shows the same seen oblique from a second plug end part, FIG. 21 shows the same mounted with cable and suction tubing, FIG. 22 is a perspective view seen oblique from a first plug end part of a second embodiment of the first coupling part for use in an electrosurgical instrument according to the present invention, FIG. 23 shows the same seen oblique from a second plug end part, FIG. 24 shows the same mounted with cable and suction tubing, FIG. 25 is a perspective view seen oblique from a first plug end part of a third embodiment of the first coupling part for use in an electrosurgical instrument according to the present invention, FIG. 26 shows the same seen oblique from a second plug end part, FIG. 27 shows the same mounted with a cable, FIG. 28 is an oblique perspective view of the second coupling part seen from the end intended for being connected to the vacuum source, FIG. 29 shows the same seen from the opposite end for being connected to the second end of the suction tubing, FIG. 30 shows a modification of the second coupling seen in the same view as in FIG. 29, FIG. 31 shows a second embodiment of an actuator for use with the present invention, and FIG. 32 shows the actuator seen directly from a short side, to illustrate the stems of the actuator buttons.

The electrosurgical instrument and switch means according to the present invention is described in more details below by way of exemplary embodiments. The electrosurgical instrument and switch means are versatile and the components of the electrosurgical instrument and switch means can be combined into a plurality of electrosurgical instrument having different properties, functionalities and designs.

Below selected embodiments are described as examples only, of the many ways the components can be combined into various electrosurgical instruments for various purposes. Functionality and design of the electrosurgical instrument can be changed either at the manufacturing stage or by the surgeon in advance of or in relation to the surgical procedure, as will be understood by the following description. Thus electrosurgical instruments comprising other combinations and arrangements of the inventive components, such as e.g. actuators, first and second coupling parts, providing the cable for connecting to the electrosurgical generator outside and/or inside the suction tubing, kinds of electrodes, and shapes of the elongated main body, and how these components are combined are also intended within the scope of the present invention.

Thus the electrosurgical instrument according to the present invention may be provided to the consumer as a kit including various components to be assembled as desired, e.g. various electrosurgical electrodes, first and/or second coupling parts and tubings of various lengths and properties, to be mounted to the elongated main body according to the surgeons choice and surgical requirements for a given surgical procedure. The surgeon is able to modify the inventive electrosurgical instrument when desired and to compose exactly the instrument he/she prefers for a given surgical patient and medical condition.

FIG. 1 shows a perspective view, seen from an actuator side, of a first embodiment of an elongated electrosurgical instrument 1 according to the present invention. The electrosurgical instrument 1 is of the kind configured for at least cutting and coagulating tissue of a patient during surgery by application of electrical energy supplied from an electrosurgical generator (not shown) to a surgical site (not shown).

The electrosurgical instrument 1 comprises a hollow elongated main body 2, a first means 3 in the form of a blade electrode 3, an actuator 4 for manual application of a force to a switch means 5 below the actuator 4, which switch means 5 is incorporated inside the elongated main body 2 and thus not visible in FIG. 1. A suction tip 6 is mounted at a first end 7 of the elongated main body 2 to surround the blade electrode 3 as well as a first suction port 40 (not visible in FIG. 1). A first embodiment of a first coupling part 8 is inserted into a second end 9 of the elongated main body 2 opposite the first end 7, which first coupling part 8 serves as an intermediate member for connecting the second end 9 of the elongated main body 2 to a first end 10 of a flexible suction tubing 11, in the present case e.g. of disposable transparent plastic material. A cable 12 is connected to the switch means 5 to deliver current from an electrosurgical generator (not shown) to the blade electrode 3 in response to actuation of the actuator 4. A logo may be provided on the elongated main body 2, as well as other kinds of decoration and information can be provided on the exterior surface of the elongated main body.

In the present embodiment of the electrosurgical instrument 1 the cable 12 extends inside the suction tubing 11 towards a second end 13 of the suction tubing 11, at which second end 13 a second coupling part 14 is mounted in order for said suction tubing 11 to be appropriately coupled to a vacuum source (not shown). In other embodiments the cable 12 can extend exterior to the suction tubing 11.

The structure and design of the elongated main body 2 is seen more clearly in the exploded, perspective, enlarged scale view of FIG. 2.

The first end 7 of the elongated main body 2 has a first opening 15 into which the first means 3, in the present case the blade electrode 3, can pass, to be mounted to the elongated main body 2, thus the combined tubular part 16 and cover part 17, in conductive communication with the switch means 5, optionally in a replaceable manner, so that the surgeon can arrange the angle of the blade electrode 3 in relation to the main body 2, as desired, or replace the blade electrode 3 with another kind of electrosurgical electrode.

The elongated main body 2 includes two main components, a tubular part 16 and a cover part 17 respectively, which parts 16,17 preferably are manufactured as individual parts which are joined, e.g. by heat sealing, in order to create the elongated main body 2, once all electrosurgical components relevant for the instrument's performance, such as switch means and wires, are mounted appropriately. The tubular part 16 and the cover part 17 may be manufactured by any suitable kind of moulding method and subsequently joined.

A wall 18 of the cover part 17 has a substantially semicircular cross-section for, inside the elongated main body 2, providing space for accommodating both the switch means 5 and at least the part of the actuator 4 that serves to engage said switch means 5. The actuator 4 protrudes only to a minimum extent beyond the outermost circumference of the wall 18 of the cover part 17, but sufficiently for the surgeon to be able to actuate the switch means 5 by using the actuator 4. The actuator 4 does not extend into the tubular part 16, which as will be described in further details later, defines a suction channel 27. In this way the overall exterior appearance of the first embodiment of the electrosurgical instrument 1 is kept elegant and slim in order not only to be easy to handle, but also to preserve a design of the electrosurgical instrument that allows said instrument to be introduced through a very small surgical incision, while at the same time obtaining an electrosurgical instrument with high suction efficiency. Other cross-sections of cover parts 17 may be appropriate too. The cover part 17 may thus be made without a perfect semicircular cross-section, e.g. be made more flat.

The wall 18 of the cover part 17 also has a first aperture part 19, through which a first actuator button 20 for application of a cutting voltage can pass in order to actuate the cutting mode of the switch means 5, and a second aperture part 21 through which a second actuator button 22 for application of a coagulation voltage can pass in order to actuate the switch means 5 in a coagulation mode of the switch means 5. An exterior side 23 of the wall 18 of the cover part 17 has protruding ribs 24, barbs or other tactile means adjacent the first aperture part 19 and the second aperture part 21. The ribs 24 extend along the longitudinal axis of the cover part 17 on both longitudinal sides of the actuator 4 in order for, on the one hand providing guidance to the surgeon for locating the actuator buttons 20,22, and on the other hand helping the surgeon to get a good hold on the elongated main body 2 during operating the electrosurgical instrument 1. Although preferred, grasping ribs 24, barbs or tactile means at the actuator's position on the main body 2 are optional.

At the first end 7 of the elongated main body 2, both the cover part 17 and the tubular part 16 have opposite facing similar circumferential engagement means 25, e.g. an external thread or spaced apart circumferentially protruding beads, for securing the suction tip 6 in adjustable manner in selected suction position in relation to the longitudinal axis of the elongated main body 2, as shown in FIG. 1. A stop web 26 defines an end position of the suction tip 6 on the elongated main body 2. Due to the stop web 26 the suction tip 6 cannot be accidentally pushed too far against the actuator 4 when adjusting the suction position of the suction tip 6. The closer the suction tip 6 gets to the stop web 26 the more of the first means, in the present case the blade electrode 3, is exposed from the suction tip 6. In this way the surgeon is able to choose the distance between the tip of the blade electrode and the suction opening of the suction tip.

The tubular part 16 constitutes a second elongated compartment of the hollow elongated main body when the tubular part 16 is assembled with the cover part 17. The tubular part 16 has a substantially semi-circular exterior wall part 28, which circumferentially merges into an elongated wall part 29 having a substantially flat base 30. The base 30 of the wall part 29 becomes the partition wall 30 of the elongated main body 2 when assembled with the cover part 17. The wall part 29 seals the second compartment from the surroundings to allow the second compartment to serve as the suction channel 27.

The partition wall 30 has guide pins 31 projecting away from the suction channel 27, for arranging the switch means 5 in the correct position in relation to the elongated main body 2, e.g. as shown in FIG. 2, closer to the first end 7 of the elongated main body 2 than to the second end 9 of said elongated main body 2. A cable trap 32, defined by a tortuous path for the cable 12, is provided on the partition wall 30 between the second end 9 of the elongated main body 2 and the projecting guide pins 31 for the switch means 5. The cable trap 32 serves to secure the cable 12 firmly inside the electrosurgical instrument 1 to prevent it from being teared off so that electrical connection to the switch means 5 accidentally is lost, e.g. when surgeons use the electrosurgical instrument 1.

Between the guide pins 31 and the first end 7 of the elongated main body 2 the tubular part 16 has a holder 33 for securing the blade electrode 3, which blade electrode 3 has a conductive coupling rod 34 that extends into a conductive electrode tip part 35 via a conductive securing part 36. The conductive securing part 36 includes a first engagement part 37 of first pentagonal cross-section, which first engagement part 37 is provided opposite a coupling end 39 of the coupling rod 34. An insulation sleeve 36a may extend axially over at least the part of the length of the securing part not including the first engagement part 37, but can also extend over the first engagement part 37, in which case the pentagonal circumference and thus the first pentagonal cross-section of the first engagement part is due to shaping of the insulation sleeve 36a. Furthermore the securing part 36 may, as shown in FIG. 2 have a scale denominator or one or more indicator lines 36b,36c to help in achieving the correct axial position of the first means 3. As will be described later with reference to e.g. FIGS. 11-14, the holder 33 of the tubular body 16 is shaped complementary to at least a longitudinal section, including the first engagement part 37, of the blade electrode 3 in order to firmly secure the blade electrode 3 or other first means correct inside the holder 33. Thus the holder 33 defines a channel 71, as seen in FIGS. 11-14, with recesses and cavities that accommodate and secure different parts or longitudinal sections of a first means 3. Accordingly, the holder 33 has a second engagement part 38 with a bore with an interior second pentagonal cross-section for engaging the first engagement part 37 of the blade electrode 3 or other first means, which first engagement part 37 has a mating first pentagonal cross-section. Thus, the first engagement part 37 and the hollow second engagement part 38 are dimensioned to mate so intimately that the orientation of the first means 3 maintains fixed during operation of the electrosurgical instrument 1. In case the electrosurgical instrument 1 is intended for use with replaceable first means 3, said first means 3 can advantageously be detachably mounted in the holder 33, and detachably coupled to the switch means 5.

The tubular part 16 can advantageously be moulded as a unit piece including a.o. the exterior wall 28, partition wall 30, protruding guide pins 31, holder 33, exterior ribs 25, and cable trap 32.

As is seen more clearly in FIG. 3, the tubular part 16 has the first suction port 40 arranged facing the first means 3 opposite a second suction port 41 at the second end 9 of the elongated main body 2.

A switch means 5 to be provided on the partition wall 30 of the tubular part 16 of the elongated main body 2 is arranged for supplying the electrical energy to the first means 3 in response to operating the actuator 4 above the switch means 5.

The switch means 5 has a first electrical contact 42, another first electrical contact 43 out of physical contact with the first electrical contact 42, and a second electrical contact 44 superjacent the first electrical contacts 42,43. Thus there is a very small distance between the plane of the first electrical contacts 42,43 and the plan of the second electrical contact 44 in the assembled state of the switch means 5, which distance defines a gap into which an insulating insert 45 is provided to prevent unintended closure of circuits and diverted current flow.

The first electrical contact 42 is activated for application of a cutting voltage by means of the first actuator button 20, and the other first electrical contact 43 is activated for application of a coagulation voltage by means of the second actuator button 21. Both first electrical contacts 42,43, the second electrical contact 44, and the insulating insert 45 has holes 46 for receiving the protruding, confronting guide pin 31 on the partition wall 30.

In this way the switch means 5 can in a very simple and fast manner be built on the partition wall 30 by stacking the very few individual components of the switch means on top of each other on the partition wall 30, connecting the cable 12 appropriately to put the switch means 5 into electrical contact with the first means 3, and enclose the switch means 5 by putting the cover part 17 on top of the tubular part 16 to define a first compartment 59a, as seen in FIGS. 4 and 18, where inside the first compartment 59a the cable 12 for putting the switch means 5 and the first means 3 in electrical communication with the electrosurgical generator extends.

By proper dimensioning of the holes 46 in the electrical contacts 42,43,44 and the diameter of the guide pins 31 on the partition wall 30, individual distances between the first electrical contacts 42,43, and well-defined gaps between any of the first electrical contacts 42,43 and the second electrical contact 44 can be defined in a simple manner. Tapered guide pins 31 can e.g. only pass through the hole 46 just to the extent where the tapered guide pin's 31 diameter's and the hole's diameter's are the same. Simply by making larger holes 46 in the second electrical contact 44, said second electrical contact 44 is able to receive e.g. the full length of the guide pins 31, while smaller holes 46 in the first electrical contacts 42,43 serve to preserve the required insulation distance between any of the first electrical contacts 42,43 and the second electrical contact 44 without the absolute requirement of inserting the insulating insert 45, although such an insulation insert 45 is preferred in most embodiments. The lateral distance between the two first electrical contacts 42,43 is obtained by corresponding suitable allocation of the guide pins 31 across the partition wall 30.

FIG. 4 is a cross-sectional view taken along line IV-IV in FIG. 1 shown without the cable 12 or any other component inside the cover part 17 to better illustrate the size of the compartments. The suction channel 27 is the second compartment of the tubular part 16, and the first compartment 59a is created when a cavity 59 of the cover part 17 is placed arching the partition wall 30 of the tubular part 16. Due to the partition wall 30 all electronic components can be kept inside the first compartment 59a isolated from the large suction channel 27. The unobstructed large cross-section of the suction channel 27 provides a very high flow velocity and therefore confers high suction performance to the electrosurgical instrument according to the present invention.

FIG. 5 is an exploded perspective view of the switch means 5, which was shown in assembled state in FIG. 2, and is seen in the perspective view in FIG. 6 with the actuator arranged aligned above.

The first electrical contact 42 has a first main body part 47 configured as a first conductive sheet component 47, the other first electrical contact 43, i.e. the second first electrical contact 43 has a second first main body part 48 configured as a second first conductive sheet component 48. The second electrical contact 44 has a second main body part 50 configured as a second conductive sheet component 50. The second conductive sheet component 50 has an electrode contacting end 51 with an electrode connection terminal 52 for securing the first means 3, and an opposite cable connection end 53 with a third wire connection terminal 54. The electrode connection terminal 52 is configured as a clamp 52 to fittingly engage the conductive coupling rod 34 of the blade electrode 3. The conductive coupling rod 34 is inserted into the electrode connection terminal 52 of the second conductive sheet component to establish electrical contact to the conductive blade electrode tip 35. In the present embodiment the electrode connection terminal 52 is illustrated as a clamp, however other designs are foreseen within the scope of the present invention.

The third wire connection terminal 54 is used for securing a third 12c of three wires of the cable 12 so that the correct voltage can be supplied to the first means 3 from an electrosurgical generator in response to a measurement of an electrical parameter representing an identification of which actuator buttons 20,22 that have been actuated. To that aspect the first 42 of the first electrical contacts 42,43 has a first wire connection terminal 55 for securing a first 12a of three wires of the cable 12, and the second 43 of the first electrical contacts 42,43 has a second wire connection terminal 56 for securing a second 12b of three wires of the cable 12. In the present case the cable 12 is a Schneider cable, where the conductor insulation is penetrated once the wire is introduced in a respective wire connection terminal.

The first conductive sheet component 47 of the first 42 of the first electrical contacts 42,43 has a raised or projecting contact part 57, and the second first conductive sheet component 48 of the second 43 of the first electrical contacts 42,43 has a raised or projecting contact part 58. The insulating insert 45 has actuating apertures 49a,49b, to allow passage of the aligned selected raised or projecting contact part 57,58 of the respective first electrical contacts 42,43 towards the second conductive sheet component 50 in response to a force application on the similarly aligned respective actuator button 20,21. When a raised or projecting contact part 57,58 touch the second conductive sheet component 50, a circuit is closed so that current of a voltage level related to the actuated actuator buttons 20,21 can flow from the electrosurgical generator to the conductive blade electrode 3 via the cable 12. No expensive optical switches or thick and complex PCB's are required. The use of simple, thin, substantially flat stacked conductive sheet components makes it possible to create a switch means 5 that appear considerable flatter than known switch means used in conventional electrosurgical instruments for similar purposes. The conductive sheets components 47,48,50 used in the inventive switch means 5 can easily be stamped, punched or cut from of thin plate, e.g. of metal. The holes for the guide pins and cutting of slits to make the raised parts can be made in the same process step. Wire connection terminals and the terminal for the first means can be made by subsequent or simultaneous bending or folding.

In the exemplary embodiment of the switch means 5 shown in FIGS. 2, 5 and 6 the first 42,43 electrical contacts have bended sides or walls, that facilitates fitting of the first electrical contacts 42,43 on the partition wall 30. Bended sides or walls are expedient when placing the sheet components on the partition wall, however not mandatory features of the first electrical contacts 42,43, but can if desired be made in the same bending process as the terminals 55,56. In case further electrical functionalities in addition to cutting and coagulation is desired implemented in the electrosurgical instrument 1 according to the present invention, more than two first electrical contacts can be included in the switch means 5, and the actuator 4 be adapted accordingly, at minimal further costs. For example, it is possible to make an electrosurgical instrument where the surgeon is able to switch between more that two voltage levels by using easy accessible buttons on the instrument instead of reaching to the electrosurgical generator simply by including an inexpensive further first electrical contact and wiring in the switch means, and corresponding actuator button.

In FIG. 6 the switch means 5 is illustrated with the actuator 4 arranged above so that the actuator buttons 20,21 are aligned with the raised or projecting parts 57,58.

FIG. 7 is a fragmentary perspective view inside the elongated opening or cavity 59 of the cover part 17 of the elongated main body 2. The switch means 5 is inserted in the cover part 17 and seen from a bottom side 60 of the second electrical contact 44. The electrode connecting terminal 52 protrudes towards the first end 7 of the elongated main body 2's cover part 17, and the coupling rod 34 of the blade electrode 3 is clamped into said electrode connecting terminal 52, while the remainder of the first means 3 extends through the holder 33 of the tubular part 16 when joined with the cover part. The switch means 5 is isolated from the suction channel and cannot get into contact with sucked matter from the surgical site. Appropriate sealing can e.g. be obtained by providing a sealing material 62 at a conductive transition 61 between the electrode connecting terminal 52 and the second conductive sheet component 50. The sealing material 62 can e.g. be provided during the process of heat-sealing the cover part 17 together with the tubular part 16. The sealing material 62 can also be provided as a transverse wall or a sealing part distal to or around e.g. the conductive transition 61. The insulation material 62 can be of the same or other plastic material as used for the elongated main body 2.

The cavity 59 of the cover part 17 has a first cable guide member 63 disposed a short distance from the second end 9 of the cover part 17 of the elongated main body 2. Proximal to the first cable guide member 63 said second end 9 is designed to receive the first coupling part 8 for providing communication to the vacuum source. In order for the cable 12 to pass smoothly without kinks inside the cover part 17 a second cable guide member 64 is made integral with the wall of the cover part 17 proximal to the first cable guide member 63. One or both of the cable guide members 63,64 can be left out if expedient or more cable guide members be included if necessary.

The elongated edges of the circumferential wall 18 of the cover part 17 has respective coupling webs 65a,66a to mate with complementary coupling webs 65b,66b, as seen in FIG. 2, on the tubular part 16 when tubular part 16 and cover part 17 are joined to create the double-lumened elongated main body. A plurality of distance members 67 is distributed inside the cavity 59 along the elongated sides to further serves to locate the tubular part 16 on the partition wall 30 correct, as well as to enforce the joined structure 16,17 and provide structural stability to the elongated main body 2.

An alternative method of joining the tubular part 16 and the cover part 17 could be gluing, however combinations of methods are within the scope of the present invention. Glue can be applied if considered expedient at any surfaces, such as e.g. at any of the coupling webs 65a,66a, the complementary coupling webs 65b,66b and the distance members 67.

FIG. 8 is a top view of the cover part 17. The actuator 4 is illustrated with different designs of actuator buttons 20,22. The differences in designs helps the surgeon to identify the correct button, and thus serves as a safety means for application either cutting voltage or coagulation voltage. The ribs 24 on both sides of the cover part 17's circumferential wall 18 next to the actuator 4 helps the surgeon to find and maintain the hand and fingers on the correct longitudinal position on the elongated main body 2. If the elongated main body 2 gets slippery the surface irregularities provided by the ribs 24 that are shaped substantially as barbs in the present embodiment prevents the surgeon from loosing his/her grip.

In the view of the cover part 17 seen in FIG. 9 the switch means has been left out, so that stems 68,69 of the first actuator button 20 and the second actuator button 22, respectively, can be seen. When the free ends of the stems 68,69 are forced towards the raised parts 57,58 of the first conductive sheets components 47,48 towards the second conductive sheet component 50 a circuit is closed and current allowed to flow to the first means, as previously described.

FIG. 10 shows the cover part seen from the side and how the stems 68,69 pass through respective first 19 and second 21 aperture halves. The very limited extent of projection of the actuator 4 away from the wall 18 of the cover part 17 is due to the very flat switch means 5 that gives the electrosurgical instrument 1a very streamlined appearance and small largest diameter. The actuator 4 is of the kind that has a common hinge 70 for the first actuator button 20 and the second actuator button 22, but other kinds of actuators having individual actuator buttons are also foreseen, as illustrated in FIGS. 30 and 31.

The first means 3 needs to be mounted or be mountable to the elongated main body in a safe manner. Longitudinal displacement or accidentally dropping out must be avoided, and the correct angular position in relation to the location of the actuator may be important to the surgeon. A hook electrode bent as an L must e.g. be positioned so that operating tip of the hook electrode faces towards the tissue when the surgeon holds the instrument in a manner that enables him/her also to operate the actuator, and thus to operate the switch means.

These problems are solved according to the present invention by providing a specially designed holder 33 at the first end 7 of the elongated main body 2.

FIG. 11 is a fragmentary, enlarged scale view of the first end 7 of the tubular part 16 encircled in FIG. 2.

The holder 33 has a holder body with a channel 71 for accommodating the blade electrode 3, and securing both the angular and axial position of said blade electrode 3 to the elongated main body 2. The second engagement part 38 of the holder 33 has an interior section crosswise the longitudinal axis of the channel of the holder. The second engagement part 38 has a second pentagonal cross-section sized to intimately engage the first pentagonal cross-section of the first engagement part 37 of the blade electrode 3. In case the electrosurgical instrument 1 is intended for use with replaceable first means 3, said first means 3 can advantageously be detachably mounted in the holder 33, thus also be detachably coupled to the switch means 5.

Each of the pentagonal cross-sections of blade electrode 3 and second engagement part 38 of holder 33, respectively, have five engaging edges thereby providing five potentially different positions and angular orientations into which a first means 3 can be placed and arranged. Conventionally first means 3 has first engagement parts 37 with hexagonal cross-section, and if the electrode tip 35 has a symmetrical design, such a conventional electrode tip can only be positioned and orientated in three different angular positions. Thus a pentagonal cross-section of the first engagement part confers more versatile positioning of in particular a first means with a symmetrical electrode tip, i.e. a symmetrical electrode tip part for cutting and coagulation of tissue.

Thus, the first engagement part 37 and the second engagement part 38 engage intimately so that the orientation of a first means 3, in this case the blade electrode 3, maintains firmly fixed during operation of the instrument. In contrast most engagement parts on conventional electrosurgical electrodes have six edges, thus they have hexagonal cross-sections. However, the more edges the more circular the cross-section becomes and the higher the risk that the electrosurgical electrode be dislocated during use, or is not placed correct during the assembling process, in particular gets angular dislocated. Engagement parts with less than five edges, e.g. having squared cross-sections, are less preferred due to the limited number of possible angular positions.

The conductive securing part 36 of the first means 3 includes the enveloping insulation sleeve 36a that improves sealing and engagement at the first opening 15 of the tubular part when the conductive securing part 36 is fitted into the hollow socket 72 of the holder 33 distal to said second engagement part 38. The conductive securing part 36 with enveloping insulation sleeve 36a has a larger cross-section or is wider than the second pentagonal cross-section of the second engagement part 38 of the holder 33, so that the securing part 36 with enveloping insulation sleeve 36a can serve as a plug or stop in a socket to thereby prevent displacement of the first means 3 in relation to the longitudinal axis of the elongated main body 2 towards the second end 9 of said elongated main body 2 so that the switch means 5 gets damaged. In summary the arrangement of the securing part 36 with enveloping insulation sleeve 36a and the socket 72 ensures the axial position and engagement of pentagonal part 37 of first means 3 and pentagonal part 38 of holder 33 in relation to each other. The pentagonal parts 38,37 of the holder 33 and first means 3, respectively, with pentagonal cross-sections serve to prevent any unintended angular dislocation or repositioning while still offering the possibility of deliberate, preselected, angular positioning of the first means 3. The holder 33 has an annular collar part 73 proximal to the pentagonal second engagement part 38 of holder 33 and a hollow connection piece 74 proximal to the annular collar part 73. The hollow connection piece 74 extends with the bore of the hollow connection piece 74 on both sides of the annular collar part 73, through said annular collar part 73, into the pentagonal second engagement part 38 of holder 33, and ends in hollow socket 72 thereby creating channel 71, with the first opening 15 at the first end 7 of the elongated main body 2 and an opposite channel entry 75, through which the coupling rod 34 of the first means 3 protrudes for engaging the electrode connection terminal 52 of the switch means 5. The first end 7 of the elongated main body 2 tapers towards the hollow socket 72 and the holder 33 can be configured to extend above the plane of the partition wall 30 to an extent that allows the first means to protrude from the opening 15 substantially concentric with the suction opening 77, as seen in FIG. 15, of the suction tip, thus so that it is ensured that electrode tip part 35 and suction tip 6 does not contact.

FIG. 12 is a sectional view taken along line XII-XII in FIG. 11 to visualize the longitudinal channel 71 of the holder 33 that serves to accommodate and secure the first means 3. The second engagement part 38 of pentagonal cross-section appears proximal to annular socket 72 and distal to annular collar part 73.

FIG. 13 is a front view inside the channel 71, seen from the tapering, hollow, annular socket 72 of the tubular part 16, prior to inserting the first means 3. FIG. 14 shows substantially the same but is a cross-sectional view taken along line XIV-XIV in FIG. 11, distal to the first suction port 40 of the tubular part 16, but seen slightly oblique from the first end 7 of the tubular part 16, in order to better see the location of the pentagonal cross-section of the second engagement part 38 of the holder 33 inside channel 71.

The suction tip 6 is seen in perspective view in FIG. 15 in front of the first suction port 40 of the elongated main body 2, which elongated main body 2 includes joined cover part 17 and tubular part 16.

The suction tip 6 has a coupling end part 76 opposite the suction opening 77. The coupling end part 76 is dimensioned to fit sealingly over the first end 7 of the elongated main body 2 to cover the first suction port 40, optionally in detachable manner. The coupling end part 76 of the suction tip 6 has a first engagement means 78 for engagement with the second engagement means 25, the circumferential second engagement means 25, as an example in form of an exterior thread, on the first end 7 of the elongated main body 2 proximal to the first suction port 40. The first engagement means 78 and the second engagement means 25 are configured so that an axial position of the suction tip 6 in relation to the first means 3 is adjustable in response to movement of the suction tip 6 about and/or along a longitudinal axis A of said suction tip 6. In a preferred embodiment the suction tip 6 is transparent to allow the surgeon to monitor, not only adjusting axial location of suction tip 6 in relation to the blade electrode 3, but also to see composition of sucked matter at any convenient point of time during surgery.

The first engagement means 78 is provided on an interior side of a circumferential coupling wall 79 of the coupling end part 76 and protrudes radially inside a bore 80 of suction tip 6 at the coupling end part 76 in order to engage the second engagement means 25 of the elongated main body 2, as is seen more clearly in FIGS. 16 and 17. The first engagement means 78 can e.g. be an interior thread, at least one annular bead, one or more spaced apart engagement elements, or combinations of the aforementioned.

The coupling end part 76 of the suction tip 6 extends via an intermediate, optionally tapering, suction part 81 into a suction end part 82 part with a tubular, non-tapering mouth 83 that ends in the suction opening 77. Other designs or modifications of the mouth 83 are intended within the scope of the present invention. The mouth 83 can e.g. have a flared skirt part (not shown) to further improve turbulence at the suction opening 77 and through the suction channel 27 out of the second end 9 of the elongated main body 2. Regarding transparency, it is most preferred that at least the suction end part 82, the intermediate suction part 81 and the mouth 83 are made of a transparent material, e.g. a plastic material that can be recycled.

The coupling end part 76 of the suction tip 6 has exterior tactile means 84 to allow the surgeon to actually feel operation of the suction tip 6 when manipulating the axial position of the suction tip 6, should he/she suddenly discover that it would be better to expose more or less of the blade electrode part 35 from the suction opening 77 at a given moment during the surgical procedure, e.g. in order to change distance of mouth 83 to the wound created by the voltage applied by the blade electrode tip part 35. Thus, not only can the surgeon operate the actuator 4 with his/hers fingers without looking at the electrosurgical instrument 1, he/she can also make a qualified adjustment of the axial position of the suction tip 6 without actually being able to see what he/she is doing because he/she knows the position of the tactile means 84, e.g. one or more ribs, beads, corrugations, indents or other uneven surface topography.

In the present exemplary embodiment the first engagement means is achieved by five spaced apart engagement elements 78a,78b,78c,78d,78e in the form of radial webs provided close to the opening at the coupling end 76 of the suction tip, as can be seen in the end view of the suction tip 6 seen in FIG. 16 inside the bore 80. Alternative engagement elements can be provided. An interior thread may e.g. serve to be screwed on the exterior thread 25 on the elongated main body 2. Just one radial web may be required to achieve the beneficial inventive adjustable engagement between suction tip and hollow elongated main body.

The interaction of the first engagement means 78 and the second engagement means 25 creates a further tactile means for adjusting and fine tuning axial position of suction tip 6 on the first end 7 of the elongated main body 2. In the present embodiment adjusting of mutual axial position between first engagement means 78 and second engagement means 25 can, as an example, be done by screwing or rotating the coupling end part 76 of the suction tip 6 onto the second engagements means 25, or by application of a small axial force to the suction tip 6, e.g. by pushing the suction tip 6 towards and away from the stop element in form of a stop web 26 on the cover part 17 of the elongated main body 2. When webs 78a, 78b, 78c, 78d, 78e snaps into valleys 85 between ribs 86 of the thread or other circumferential projections of the second engagement means 25 the surgeon can easily feel it. So the surgeon easily experiences displacement or adjusting actions. Pushing the suction tip 6 may be preferred in preference to or in combination with rotation for initial adjusting and fine adjustment, but it is up to the surgeon to decide if rotation or axial force application are most preferred, e.g. in dependency of the surgical condition and spatial limitations and requirements. Embodiments including just on radial web are contemplated within the scope of the present invention.

The enlarged scale view of FIG. 17 shows a fragment of the first end 7 of the tubular part 16 with the suction tip mounted at the elongated main body 2 to illustrate how the exterior tactile means 84 of the suction tip is arranged encircling the first engagement means 25. Only one of the webs 78, namely web 78e can be seen in FIG. 17. Web 78e engages valley 85 to ensure the axial position in relation to the second engagement means 25.

The second end 9 of the elongated main body 2 could, as conventional electrosurgical instruments be adapted to be directly coupled to the vacuum source. It is however intended that the electrosurgical instrument 1 can be used with the cable outside the suction tubing, the cable inside the suction tubing or without the suction tubing.

To that aspect the electrosurgical instrument or the assembly kit for the electrosurgical instrument may, e.g. as an accessories comprise one or more different first coupling parts designed for fitting into the second coupling end 9 of the elongated main body 2, which second coupling end 9 is seen in FIG. 18. The cable 12 is bedded in second cable guide member 64 of the cover part 17 and emerges from a first click-in opening 87 of the elongated first compartment 59a at the second end 9 of the elongated main body 2 above a second click-in opening 88 of the suction channel 27.

FIG. 19 is a perspective view seen oblique from a first plug end part 89 of a first embodiment of the first coupling part 8 used in the electrosurgical instrument 1 seen in FIG. 1, and FIG. 20 is the same seen from the opposite end.

The first plug end part 89 has a first end-closed click-in part for engaging, e.g. by force-fitting into frictional engagement, and closing off the first click-in opening 87 of the elongated first compartment 59a. Below the first end-closed click-in part 90 the first plug end part 89 has a hollow second click-in part 91 for engaging the second click-in opening 88 of the suction channel 27, to thereby allow suction from the surgical site to a waste receptacle.

The first plug end part 89 extends via a circumferential collar 92 into a bevelled second plug end part 93 that fits into the first end 10 of the suction tubing 11. Coupling barbs 94 is provided on the exterior side of the second plug end part 93 to prevent unintended detachment of the suction tubing 11 once connected.

The circumferential collar 92 has substantially the same outline as or slightly larger than the outline of the second end 9 of the elongated main body 2. The collar 92 serves to end fit said elongated main body 2, as well as a stop for the suction tubing 11.

The hollow second click-in part 91 has a suction inlet 95 that extends into the bore 96 of the second plug end part 93 towards a suction outlet 97 thereby allowing passage of sucked matter from the elongated main body 2, through the first coupling part 8, and into the suction tubing 11.

A first cable groove 98 is provided in the first plug end part 89 to receive the cable 12 when the first end-closed click-in part 90 is mounted inside the first click-in opening 87. The first cable groove 98 becomes substantially axially aligned with a corresponding cable groove of at least any of the first and second cable guide members 63,64 of the cover part 17, to allow the cable 12 to pass in recessed manner and the suction tubing 11 to be mounted to surround the cable 12. When using the first embodiment of a first coupling part 8 the cable 12 passes inside the suction tubing 11, as is seen more clearly in FIG. 21.

FIGS. 22 and 23 show a second embodiment of a first coupling part 8' that corresponds substantially to the first coupling part 8, and for like parts same reference numerals are used.

The second embodiment of a first coupling parts 8' is modified in that the circumferential collar 92' is thicker, i.e. has a longer axial extent, and that the first cable groove 98' ends blind in the circumferential collar 92' to enable exit of the cable 12 at this location, as illustrated in FIG. 24.

FIGS. 25 and 26 show a third embodiment of a first coupling part 8" for use in an elongated main body 2 according to the present invention. The third embodiment of a first coupling part 8" has a modified first plug end part 89', and for like parts same reference numerals are used.

The first plug end part 89" has a first end-closed click-in part 90" for engaging, e.g. by force-fitting into frictional engagement, and closing off the first click-in opening 87 of the elongated first compartment 59a. Below the first end-closed click-in part 90" the first plug end part 89" has a blind second click-in part 99 for engaging the second click-in opening 88 of the suction channel 27, to thereby close the suction channel 27 and allow the electrosurgical instrument 1 to be used without suction, thus as a simple electrosurgical pencil if desired.

In a manner similar to the first cable groove 98 of the first embodiment of the first end-closed click-in part 90, the first cable groove 98" extends into the first end-closed click-in part 90" through the circumferential collar 92" where the first cable groove 98" exits into a bevelled second plug end part 93" that is end capped by base surface, wall part or cap 100.

FIG. 27 shows the third embodiment of a first coupling part 8" with a cable 12 arranged inside the first cable groove 98", thus the suction channel 27 will be closed by the second plug end part 93".

FIG. 28 is an oblique perspective view of the second coupling part 14 seen from a vacuum source coupling end part 101, i.e. from the end intended for being connected to the vacuum source.

The vacuum source coupling end part 101 has two concentric tubes, an inner tube 102 and an outer tube 103 of larger internal diameter than the inner tube 102. Due to the different diameters of the tubes 102,103 the second coupling part 14 can be connected to vacuum sources having vacuum connection pieces of two different sizes. Use of the second coupling part therefore facilitates use of the electrosurgical instrument according to the present invention, as well as other medical devices that requires connection to a vacuum source, using one and the same second coupling part 14. Accordingly, often it is not necessary to invest in new vacuum sources or adapters for being able to make use of suction from a conventional vacuum source.

The vacuum source coupling end part 101 extends into the suction tubing end part 104 defined by an annular wall 105 with a second cable groove 106 and serrations 107. The cable groove 105 is provided in a manner similar to the first cable groove 98 of the first coupling end part 8 to allow the cable 12 to exit the suction tubing 11 just in form of vacuum source coupling end part 101, i.e. close to the vacuum source. A evacuation channel 108 extends via the inner tube 102 and into suction tubing end part 104, as seen in FIG. 29 that shows the second coupling part from the end to be connected to the second end 13 of the suction tubing 11.

In a modified embodiment of the second coupling part 14 no second cable groove 105 is provided. The modified second coupling part 14 without second cable groove 106 is suited for use with for example the second embodiment of the first coupling part 8".

A modification of a second coupling part is shown in FIG. 30. The modified second coupling part corresponds to the embodiment shown in FIGS. 28 and 29 and for like parts same reference numerals are used. The modified second coupling part 14 only differs in that outer tube 103 has one or more slots 109 extending from the free end 110 and inside the other tube. Due to the one or more slots 109, of which only one is shown in FIG. 30, the circumferential skirt that defines the wall of the outer tube is split to allow the sides of the slots to overlap and reduce the diameter of the outer tube, so that the outer tube can be compacted to be inserted into a connection piece instead of surrounding the connection piece. The second coupling parts according to the present invention thus fit standard connection pieces of many different diameters.

A second embodiment of an actuator 4' is seen in FIG. 31. The actuator corresponds substantially to the first embodiment of an actuator 4, and for like part same reference numerals are used. The first embodiment of an actuator 4' is configured as a rocker with opposite rocker arms merging into each other. In contrast the second embodiment of an actuator 4' has no rocker arm. Instead the actuator buttons 20',22' is provided as separate parts with respective stem 68',69'. The buttons 20',22' has different height and surface texture and/or surface to enable the surgeon to identify the relevant button, as seen more clear in the view of FIG. 32, where the second embodiment of an actuator 4' is seen from the left side of FIG. 31.

The present invention proposes a very versatile system to make customised electrosurgical instruments at low costs due to the many separate components that can be combined in multiple ways.

The person skilled in the art will understand that within the scope of the present invention the vacuum source can be replaced with a fluid source for delivering a fluid to a surgical site through the suction tubing. Thus instead of evacuating and aspirating from a surgical site, a liquid, such as saline, can be delivered. The electrosurgical instrument can even have a multiple-lumen channel for coupling with a first coupling means having a corresponding number of hollow protruding legs to be clicked-in. Thus first couplings means adapted for both irrigation and suction may be contemplated within the scope of the present invention.

The invention claimed is:

1. An electrosurgical instrument for connecting to a vacuum source having a first vacuum connection piece and a second vacuum connection piece, the first vacuum connection piece having a different size from the second vacuum connection piece, the electrosurgical instrument comprising:
   an electrode configured to perform electrosurgery;
   an elongated main body having a first end and an opposite second end, the elongated main body defining a suction channel that is in fluid communication with a suction tubing and the vacuum source, the first end of the elongated main body securing the electrode; and
   a coupler including a first coupling part configured to fit into the second end of the elongated main body and a second coupling part;
   wherein the second coupling part includes a suction tubing end part for connection to the suction tubing and a vacuum coupling end part for connection to the vacuum source; and
   wherein the vacuum coupling end part includes an inner tube and an outer tube, the inner tube for connecting the suction tubing to the first vacuum connection piece, and the outer tube for connecting to the second vacuum connection piece;
   wherein the outer tube surrounds the inner tube, with the inner tube and the outer tube being concentric with one another, each one of the outer tube and the inner tube having an internal diameter and an external diameter, and the internal diameter of the outer tube being larger than the internal diameter of the inner tube;
   wherein the inner and outer tubes are radially spaced apart from one another by a gap between the inner and outer tubes, with the gap capable of receiving one of the vacuum connection pieces when aligned with the gap between the inner and outer tubes;
   wherein the outer tube has at least one longitudinal slot that comprises opposite free edges that are configured to overlap one another to reduce the diameter of the outer tube so that the outer tube can be compacted to be inserted into the second connection piece.

2. The electrosurgical instrument according to claim 1, wherein any of the first coupling part and the second coupling part are detachable.

3. The electrosurgical instrument according to claim 1, wherein the suction tubing end part has an annular wall with a cable groove.

4. The electrosurgical instrument according to claim 1, wherein the inner and outer tubes are coextensive in length with one another.

5. The electrosurgical instrument according to claim 4, wherein the inner and outer tubes are concentric about a common axis, with the inner and outer tubes having free ends terminating at a common plane orthogonal to said common axis.

6. The electrosurgical instrument according to claim 1, further comprising a cable partially confined within the suction tubing and configured to deliver current to the electrode.

7. An electrosurgical instrument for connecting to a vacuum source having a first vacuum connection piece and a second vacuum connection piece, the first vacuum connection piece having a different size from the second vacuum connection piece, the electrosurgical instrument comprising:
   an elongated main body having a first end and an opposite second end, the elongated main body defining a suction channel that is in fluid communication with a suction tubing and the vacuum source, the first end of the elongated main body for securing an electrode, and wherein the suction tube comprises a cable partially confined within the suction tubing;
   a coupler including a first coupling part configured to fit into the second end of the elongated main body and a second coupling part;
   wherein the second coupling part includes a suction tubing end part for connection to the suction tubing and a vacuum coupling end part for connection to the vacuum source; and
   wherein the vacuum coupling end part includes an inner tube and an outer tube, the inner tube for connecting the suction tubing to the first vacuum connection piece, and the outer tube for connecting to the second vacuum connection piece;
   wherein the outer tube surrounds the inner tube, with the inner tube and the outer tube being concentric with one another, each one of the outer tube and the inner tube having an internal diameter and an external diameter, and the internal diameter of the outer tube being larger than the internal diameter of the inner tube;
   wherein the inner and outer tubes are radially spaced apart from one another by a gap between the inner and outer tubes, with the gap capable of receiving one of the vacuum connection pieces when aligned with the gap between the inner and outer tubes;
   wherein the outer tube has at least one longitudinal slot that comprises opposite free edges that are configured to overlap one another to reduce the diameter of the outer tube so that the outer tube can be compacted to be inserted into the second connection piece.

8. An electrosurgical instrument for connecting to a vacuum source having a first vacuum connection piece and a second vacuum connection piece, the first vacuum connection piece having a different size from the second vacuum connection piece, the electrosurgical instrument comprising:

an elongated main body having a first end and an opposite second end, the elongated main body defining a suction channel that is in fluid communication with a suction tubing and the vacuum source, the first end of the elongated main body for securing an electrode;

a switch and an associated actuator to control application of electrical energy to the electrode;

a coupler including a first coupling part configured to fit into the second end of the elongated main body and a second coupling part;

wherein the second coupling part includes a suction tubing end part for connection to the suction tubing and a vacuum coupling end part for connection to the vacuum source; and wherein the vacuum coupling end part includes an inner tube and an outer tube, the inner tube for connecting the suction tubing to the first vacuum connection piece, and the outer tube for connecting to the second vacuum connection piece;

wherein the outer tube surrounds the inner tube, with the inner tube and the outer tube being concentric with one another, each one of the outer tube and the inner tube having an internal diameter and an external diameter, and the internal diameter of the outer tube being larger than the internal diameter of the inner tube;

wherein the inner and outer tubes are radially spaced apart from one another by a gap between the inner and outer tubes, with the gap capable of receiving one of the vacuum connection pieces when aligned with the gap between the inner and outer tubes;

wherein the outer tube has at least one longitudinal slot that comprises opposite free edges that are configured to overlap one another to reduce the diameter of the outer tube so that the outer tube can be compacted to be inserted into the second connection piece.

* * * * *